(12) United States Patent
Valenzano et al.

(10) Patent No.: US 10,512,677 B2
(45) Date of Patent: *Dec. 24, 2019

(54) HIGH CONCENTRATION ALPHA-GLUCOSIDASE COMPOSITIONS FOR THE TREATMENT OF POMPE DISEASE

(71) Applicant: Amicus Therapeutics, Inc., Cranbury, NJ (US)

(72) Inventors: Kenneth Valenzano, East Brunswick, NJ (US); John Crowley, Princeton, NJ (US); Richie Khanna, Somerset, NJ (US); John Flanagan, East Windsor, NJ (US)

(73) Assignee: Amicus Therapeutics, Inc., Cranbury, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/015,556

(22) Filed: Jun. 22, 2018

(65) Prior Publication Data

US 2018/0360928 A1    Dec. 20, 2018

Related U.S. Application Data

(60) Division of application No. 15/192,137, filed on Jun. 24, 2016, now Pat. No. 10,046,033, which is a continuation of application No. 14/379,131, filed as application No. PCT/US2013/029660 on Mar. 7, 2013, now Pat. No. 9,404,100.

(60) Provisional application No. 61/750,718, filed on Jan. 9, 2013, provisional application No. 61/607,920, filed on Mar. 7, 2012.

(51) Int. Cl.

| | |
|---|---|
| *A61K 47/22* | (2006.01) |
| *A61K 38/47* | (2006.01) |
| *C12N 9/96* | (2006.01) |
| *A61K 9/00* | (2006.01) |
| *A61K 31/7008* | (2006.01) |
| *A61K 31/445* | (2006.01) |
| *C12N 9/26* | (2006.01) |

(52) U.S. Cl.
CPC ............ *A61K 38/47* (2013.01); *A61K 9/0019* (2013.01); *A61K 31/445* (2013.01); *A61K 31/7008* (2013.01); *A61K 47/22* (2013.01); *C12N 9/2408* (2013.01); *C12N 9/96* (2013.01); *C12Y 302/0102* (2013.01)

(58) Field of Classification Search
None
See application file for complete search history.

(56) References Cited

U.S. PATENT DOCUMENTS

| | | | |
|---|---|---|---|
| 4,837,237 A | 6/1989 | Rohrschneider et al. | |
| 4,985,445 A | 1/1991 | Tsuruoka et al. | |
| 5,011,829 A | 4/1991 | Hirsch et al. | |
| 5,103,008 A | 4/1992 | Scudder et al. | |
| 5,236,838 A | 8/1993 | Rasmussen et al. | |
| 5,399,567 A | 3/1995 | Platt et al. | |
| 5,472,969 A | 12/1995 | Platt et al. | |
| 5,580,757 A | 12/1996 | Desnick et al. | |
| 5,786,369 A | 7/1998 | Platt et al. | |
| 5,801,185 A | 9/1998 | Platt et al. | |
| 5,879,680 A | 3/1999 | Ginns et al. | |
| 6,083,725 A | 7/2000 | Selden et al. | |
| 6,118,045 A | 9/2000 | Reuser et al. | |
| 6,210,666 B1 | 4/2001 | Miyamura | |
| 6,225,325 B1 | 5/2001 | Jacob | |
| 6,274,597 B1 | 8/2001 | Fan et al. | |
| 6,395,884 B1 | 5/2002 | Selden et al. | |
| 6,451,600 B1 | 9/2002 | Rasmussen et al. | |
| 6,458,574 B1 | 10/2002 | Selden et al. | |
| 6,461,609 B1 | 10/2002 | Calhoun et al. | |
| 6,465,488 B1 | 10/2002 | Butters et al. | |
| 6,534,300 B1 | 3/2003 | Canfield | |
| 6,537,785 B1 | 3/2003 | Canfield | |
| 6,545,021 B1 | 4/2003 | Mueller et al. | |
| 6,583,158 B1 | 6/2003 | Fan et al. | |
| 6,589,964 B2 | 7/2003 | Fan et al. | |
| 6,599,919 B2 | 7/2003 | Fan et al. | |
| 6,696,059 B2 | 2/2004 | Jacob et al. | |
| 6,916,829 B2 | 7/2005 | Fan et al. | |
| 7,141,582 B2 | 11/2006 | Fan et al. | |
| 7,351,410 B2 | 4/2008 | van Bree et al. | |
| 7,371,366 B2 | 5/2008 | Canfield | |
| 7,396,811 B2 | 7/2008 | LeBowitz et al. | |
| 7,560,424 B2 | 7/2009 | LeBowitz et al. | |
| 7,655,226 B2 | 2/2010 | Van Bree et al. | |
| 7,658,916 B2 | 2/2010 | Zhu et al. | |
| 7,785,856 B2 | 8/2010 | LeBowitz et al. | |
| 7,858,576 B2 | 12/2010 | LeBowitz et al. | |
| 7,910,545 B2 | 3/2011 | Meeker et al. | |
| 7,981,864 B2 | 7/2011 | LeBowitz | |
| 8,940,766 B2 | 1/2015 | Boyd et al. | |
| 9,056,101 B2 | 6/2015 | Lockhart et al. | |
| 9,181,184 B2 | 11/2015 | Mugrage et al. | |

(Continued)

FOREIGN PATENT DOCUMENTS

| | | |
|---|---|---|
| EP | 1137762 B1 | 10/2008 |
| EP | 2020438 A1 | 2/2009 |

(Continued)

OTHER PUBLICATIONS

Lembcke et al., Lysosomal storage of glycogen as a sequel of alpha-glucosidase inhibition by the absorbed deoxynojirimycin derivative emiglitate (BAYo1248). A drug-induced pattern of hepatic glycogen storage mimicking Pompe's disease (glycogenesis type II). Res. Exp. Med., 1991; 191(6): 389-404.

(Continued)

*Primary Examiner* — Thane Underdahl
(74) *Attorney, Agent, or Firm* — Finnegan, Henderson, Farabow, Garrett & Dunner, LLP

(57) ABSTRACT

The present application provides for compositions comprising high concentrations of acid a-glucosidase in combination with an active site-specific chaperone for the acid α-glucosidase, and methods for treating Pompe disease in a subject in need thereof, that includes a method of administering to the subject such compositions. The present application also provides methods for increasing the in vitro and in vivo stability of an acid α-glucosidase enzyme formulation.

15 Claims, 30 Drawing Sheets

(56) References Cited

U.S. PATENT DOCUMENTS

| | | |
|---|---|---|
| 2002/0049233 A1 | 4/2002 | Kararli et al. |
| 2002/0095135 A1 | 7/2002 | Meeker et al. |
| 2004/0180419 A1 | 9/2004 | Fan |
| 2004/0204379 A1 | 10/2004 | Cheng et al. |
| 2005/0244400 A1 | 11/2005 | LeBowitz et al. |
| 2006/0121018 A1 | 6/2006 | LeBowitz |
| 2006/0264467 A1 | 11/2006 | Mugrage et al. |
| 2007/0178081 A1 | 8/2007 | Fan |
| 2009/0117091 A1 | 5/2009 | LeBowitz et al. |
| 2009/0203575 A1 | 8/2009 | LeBowitz et al. |
| 2010/0119502 A1 | 5/2010 | Do et al. |
| 2010/0260740 A1 | 10/2010 | Boyd et al. |
| 2011/0136151 A1 | 6/2011 | Wustman et al. |
| 2011/0189710 A1 | 8/2011 | Wustman et al. |

FOREIGN PATENT DOCUMENTS

| | | |
|---|---|---|
| FR | 2861991 | 5/2005 |
| WO | WO-2000/034451 A1 | 6/2000 |
| WO | WO-2001/019955 A2 | 3/2001 |
| WO | WO-2004/069190 A2 | 8/2004 |
| WO | WO-2005/077093 A2 | 8/2005 |
| WO | WO-2006/125141 A3 | 9/2007 |
| WO | WO-2008/112525 A2 | 9/2008 |
| WO | WO-2009/066069 A1 | 5/2009 |
| WO | WO-2010/015816 A2 | 2/2010 |
| WO | WO-2010/148253 A2 | 12/2010 |

OTHER PUBLICATIONS

Mellor, Howard R., et al., Cellular effects of deoxynojirimycin analogues; uptake, retention and inhibition of glycosphingolipid biosynthesis. Biochem J. 2004; 381:861-866.

National Institutes of Health Clinical Center. Patient Education: Giving a subcutaneous injection. Bethesda, MD: NIH Clinical Center, 2002, 3 pages.

Non-Final Office Action in U.S. Appl. No. 14/379,131, dated Sep. 15, 2015, 14 pages.

Parenti, G., et al., Alpha-Glusosidase Enhancement in Fibroblasts from Patients with Pompe Disease. J. Inherit. Metab. Dis. 2005: 28:193, Abstract 383-P.

PCT International Search Report in PCT/US2013/29660, dated May 8, 2013, 2 pages.

Platt, et al. Prevention of Lysosomal Storage in Tay-Sachs Mice Treated with N-butyldeoxynojirimycin. Science, 1997; 276:428-431.

Porto et al. The Pharmacological Chaperone N-butyldeoxynojirimycin Enhances Enzyme Replacement Therapy in Pompe Disease Fibroblasts. Mol Ther., 2009;17(6):964-71.

Raben et al., Replacing acid alpha-glucosidase in Pompe disease: recombinant and transgenic enzymes are equipotent, but neither completely clears glycogen from type II muscle fibers. Mol Ther., 2005; 11(1):48-56.

Ruvinov et al., Monovalent Cations Partially Repair a Conformational Defect in a Mutant Tryptophan Synthase $\alpha 2\beta 2$ Complex ($\beta$-E109A). J. Biol. Chem., 1995; 270:17333-38.

Van der Ploeg et al., Receptor-Mediated Uptake of Acid $\alpha$-Glucosidase Corrects Lysosomal Glycogen Storage in Cultured Skeletal Muscle, Pediatric Research, 1988; 24(1):90-94.

Van Hove et al., High-level production of recombinant human lysosomal acid $\alpha$-glucosidase in Chinese hampster ovary cells which targets to heart muscle and corrects glycogen accumulation in fibroblasts from patients with Pompe disease. Proc. Natl. Acad. Sci., 1996; 93:65-70.

Van Hove et al., Purification of recombinant human precursor acid $\alpha$-glucosidase. Biochem. Mol. Biol. Int. 1997: 43(3):613-23.

Wilson, B.A. et al., Medication Administration Techniques. Prentice Hall Nurse's Drug Guide 2003. Companion Website [online]. Retrieved Sep. 30, 2014 from: http://wps.prenhall.com/chet_wilson_drugguides_1/6/1576/403558_cw/index.html, 1 page.

Anthropometric Reference Data for Children and Adults: United States, 2007-2010, Vital and Health Statistics, Series 11, No. 252, U.S. Department of Health and Human Services, Center for Disease Control, Oct. 2012, 48 pages.

Asano et al., Nitrogen-in-the-ring pyranoses and furanoses: structural basis of inhibition of mammalian glycosidases. J. Med. Chem. 1994; 37:3701-06.

Banati et al., Enzyme replacement therapy induces T-cell responses in late-onset Pompe disease. Muscle Nerve. Nov. 2011, 44(5):720-6.

Barton et al., Replacement Therapy for Inherited Enzyme Deficiency—Macrophage-Targeted Glucocerebrosidase for Gaucher's Disease. N. Eng. J. Med. 1991; 324:1464-1470.

Butters, et al. Imino Sugar Inhibitors for Treating the Lysosomal Glycosphingolipidoses. Glycobiology, 2005; 15(10):43E-52R.

Courageot et al., $\alpha$-Glucosidase inhibitors reduce dengue virus production by affecting the initial steps of virion morphogenesis in the endoplasmic reticulum. Journal of Virology, 2000, 74:564-572.

Cox et al., Novel oral treatment of Gaucher's disease with N-butyldeoxynojirimycin (OGT 918) to decrease substrate biosynthesis. The Lancet, 2000; 355:1481-1485.

Dale et al., Reversible inhibitors of beta-glucosidase. Biochemistry 1985; 24:3530-39.

Duke University, *Duke Obtains FDA Designation for Pompe Disease Therapy*. Press release, dated Sep. 2, 1997, 2 pages.

Genzyme Corporation. Myozyme®. Prescribing Information; Jun. 2010, 3 pages.

Jeyakumar et al. Delayed symptom onset and increased life expectancy in Sandhoff disease mice treated with N-butyldeoxynojirimycin, Proc. Acad. Sci. USA. 1999; 96:6388-6393.

Khanna et al., The pharmacological chaperone AT2220 increases recombinant human acid $\alpha$-glucosidase uptake and glycogen reduction in a mouse model of Pompe disease. PLoS ONE, 2012; 7(7):e40776.

Kishnani et al., Duvolustat HCI Increases Systemic and Tissue Exposure of Active Acid $\alpha$-Glucosidase in Pompe Patients Co-administered with Alglucosidase $\alpha$. Molecular Therapy, 2017; 25(5):1199-1208.

Klinge et al., Enzyme replacement therapy in classical infantile pompe disease: results of a ten-month follow-up study. Neuropediatrics, 2005; 36(1):6-11.

Legler et al., Synthesis of 5-amino-5-deoxy-D-galactopyranose and 1,5-dideoxy-1,5-imino-D-galactitol, and their inhibition of alpha- and beta-D-galactosidases. Carbohydrate Res. 1986: 155:119-29.

Myozyme® uptake in Heart and Diaphragm Tissue when Administered with and without 1-DNJ-HCl (y-axis in both figures denotes GAA Activity (nmol/mg protein/hr)

The effect of Myozyme administration once every other week for up to 8 weeks on tissue uptake and glycogen clearance in GAA KO mice when administered alone or in combination with 1-DNJ-HCl.

- Myozyme administered at 40 mg/kg via tail vein injection (IV)
- 1-DNJ-HCl administered at 30 mg/kg 30 min prior to Myozyme via oral gavage (PO)
- Before the third and fourth injection, 10 mg/kg of diphenhydramine (DPH) administered intraperitoneally (IP)
- Mice sacrificed 14 days post-Myozyme injection
- Myozyme uptake assessed by activity, Western blotting & glycogen assay

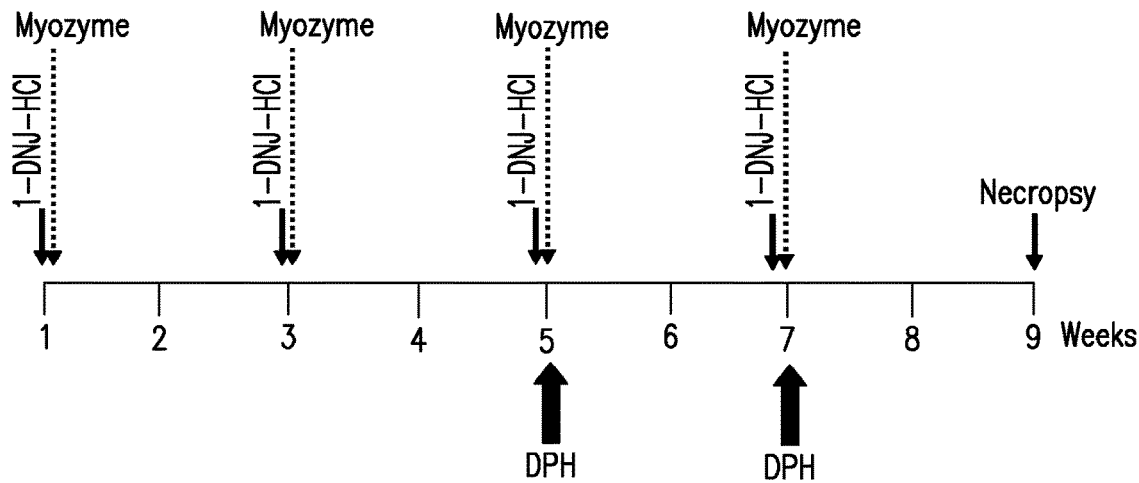

FIG. 10

1-Deoxynojirimycin (DNJ) Reduces Myozyme Aggregation at Neutral pH/37°C

| Myozyme | − | + | + |
|---|---|---|---|
| DNJ | − | − | + |

Incubations set-up in phosphate-buffered saline at pH 7.4 −/+ 1 mM DNJ

Aggregation assessed after 4 weeks at 37°C

*p<0.05 vs control, #p<0.05 vs rhGAA alone

Plasma GAA levels 2 hours after SQ dose

GAA, set 1

GAA, set 2

*p<0.05 vs control, #p<0.05 vs rhGAA alone
Western blot: 2 mice from each group.   3A6-1F2 antibody Plasma GAA levels 4 hours after SQ dose

*$p<0.05$ vs control, #$p<0.05$ vs rhGAA alone
Western blot: 2 mice from each group. 3A6-1F2 antibody

HIGH CONCENTRATION ALPHA-GLUCOSIDASE COMPOSITIONS FOR THE TREATMENT OF POMPE DISEASE

CROSS REFERENCE TO RELATED APPLICATIONS

This is a divisional of U.S. Non-Provisional application Ser. No. 15/192,137, filed Jun. 24, 2016, which is a continuation of U.S. Non-provisional application Ser. No. 14/379,131, filed Aug. 15, 2014, which is the national stage entry of PCT/US13/29660, filed Mar. 7, 2013, which claims the benefit of U.S. Provisional Application No. 61/607,920 filed Mar. 7, 2012 and U.S. Provisional Application No. 61/750,718 filed Jan. 9, 2013, to each of which priority is claimed and each of which are incorporated herein by reference in their entireties.

1. INTRODUCTION

The present invention relates to methods of treating, preventing, and/or ameliorating Pompe Disease. The present invention also relates to compositions and medicaments which may be labeled for use in the treatment of Pompe Disease.

2. BACKGROUND OF THE INVENTION

Pompe disease (acid maltase deficiency) is caused by a deficiency in the enzyme acid α-glucosidase (GAA). GAA metabolizes glycogen, a storage form of sugar used for energy, into glucose. The accumulation of glycogen leads to progressive muscle myopathy throughout the body which affects various body tissues, particularly the heart, skeletal muscles, liver, and nervous system. According to the National Institute of Neurological Disorders and Stroke, Pompe disease is estimated to occur in about 1 in 40,000 births.

There are three recognized types of Pompe disease—infantile, juvenile, and adult onset (see, e.g., Hirschhorn and Reuser, In: Scriver C R, Beaudet A L, Sly W, Valle D, editors; The Metabolic and Molecular Bases of Inherited Disease, Vol. III, New York: McGraw-Hill; 2001. p. 3389-420, 2001: 3389-3420). Infantile-onset Pompe Disease is the most severe, and presents with symptoms that include severe lack of muscle tone, weakness, enlarged liver and heart, and cardiomyopathy. Swallowing may become difficult and the tongue may protrude and become enlarged. Most children die from respiratory or cardiac complications before the age of two, although a sub-set of infantile-onset patients live longer (non-classical infantile patients). Juvenile onset Pompe disease first presents in early to late childhood and includes progressive weakness of the respiratory muscles in the trunk, diaphragm, and lower limbs, as well as exercise intolerance. Most juvenile onset Pompe patients do not live beyond the second or third decade of life. Adult onset symptoms involve generalized muscle weakness and wasting of respiratory muscles in the trunk, lower limbs, and diaphragm. Some adult patients are devoid of major symptoms or motor limitations.

Unless identified during pre-natal screening, diagnosis of Pompe disease is a challenge. Diagnosis of adult-onset Pompe is even more difficult since number, severity, and type of symptoms a patient experiences vary widely, and may suggest more common disorders such as muscular dystrophies. Diagnosis is confirmed by measuring α-glucosidase activity and/or detecting pathologic levels of glycogen from biological samples. Currently the only approved therapy is enzyme replacement therapy with recombinant α-glucosidase.

Pompe disease is one of several of glycogen pathologies. Others include Debrancher deficiency (Cori's-Forbes' disease; Glycogenosis type III); Branching deficiency (Glycogenosis type IV; Andersen's disease); Myophsophorylase (McArdle's disease, Glycogen storage disease V); Phosphofructokinase deficiency-M isoform (Tauri's disease; Glycogenosis type VII); Phosphorylase b Kinase deficiency (Glycogenosis type VIII); Phosphoglycerate kinase A-isoform deficiency (Glycogenosis IX); Phosphoglycerate M-mutase deficiency (Glycogenosis type X).

3. SUMMARY OF THE INVENTION

The present invention relates to methods for the treatment of Pompe Disease (e.g., infantile-onset Pompe disease), by administering to an individual in need of such treatment an acid α-glucosidase (GAA) enzyme, (e.g., a recombinant human GAA (rhGAA)) in combination with an Active Site-Specific Chaperone (ASSC) for the GAA enzyme (e.g., 1-deoxynojirimycin (DNJ, 1-DNJ)).

The present invention further provides a method of increasing the stability of a GAA enzyme in a proper conformation, in vivo and in vitro. In one embodiment, an acid α-glucosidase (GAA) enzyme (e.g., a recombinant human GAA (rhGAA)) in combination with an ASSC for the GAA enzyme (e.g., 1-deoxynojirimycin or 1-deoxynojirimycin-HCl) is administered to an individual in need of such treatment. The GAA enzyme is stabilized conformationally when combined with an ASSC and is well-suited to withstand, for example, thermal and pH challenges.

In certain embodiments, the GAA enzyme is combined with an ASSC at a high concentration, for example, at a concentration between about 5 and about 250 mg/mL.

In certain embodiments, the GAA enzyme is combined with an ASSC at a high concentration, for example, at a concentration selected from the group consisting of about 25 mg/mL, about 80 mg/mL, about 115 mg/mL, about 160 mg/mL, about 200 mg/mL and about 240 mg/mL.

In certain embodiments, the GAA enzyme is combined with an ASSC, wherein the ASSC is present at a concentration between about 5 mg/mL and about 200 mg/mL.

In certain embodiments, the GAA enzyme is combined with an ASSC, wherein the ASSC is present at a concentration selected from the group consisting of about 32 mg/mL and about 160 mg/mL.

In certain embodiments, the GAA enzyme is combined with an ASSC, wherein the ASSC is present at a concentration between about 0.5 mM and about 20 mM.

In certain embodiments, the GAA enzyme is combined with an ASSC as a co-formulation.

In certain embodiments, the GAA enzyme is combined with an ASSC in a co-formulation, wherein the co-formulation further comprises an excipient. In certain embodiments, the excipient is selected from the group consisting of polyethylene glycol (PEG), PEG-400, arginine, arginine and glutamic acid, proline, gamma-cyclodextrin and combinations thereof.

In certain embodiments, the formulations of the invention maintain physical and chemical stability over extended periods despite the high concentration of protein, and have a viscosity suitable for subcutaneous administration. The formulations of the invention are established, at least in part, on the surprising finding that a GAA enzyme combined with an ASSC can remain soluble at a high concentration (e.g., 25 mg/mL) and remain non-aggregated while maintaining a viscosity suitable for injection (e.g., subcutaneous administration).

In certain embodiments, the compositions of the present invention comprise more than about 5 mg/mL of GAA enzyme.

In certain embodiments, the compositions of the invention comprise about 25 mg/mL GAA enzyme and about 10 mM DNJ.

In certain embodiments, the compositions of the invention comprise about 25 mg/mL GAA enzyme and about 1 mM DNJ.

An advantage of the formulation of the invention is that it provides a high concentration of protein without increased protein aggregation, which commonly occurs with increased protein concentration. In one embodiment, the formulation of the invention has less than about 1% aggregate protein.

According to one aspect of the invention, methods of enhancing delivery of GAA to tissues, for example muscle tissue, of an individual with Pompe disease are provided. The methods include administering GAA in combination with an ASSC subcutaneously to the individual. In some embodiments, the GAA in combination with an ASSC is administered in a sufficient dose to result in a peak concentration of GAA in tissues of the subject within about 24 hours after the administration of the dose. In certain embodiments, the GAA in combination with an ASSC is administered in a sufficient dose to result in a peak concentration of GAA in tissues of the subject within about 10 to about 50 hours, or about 45, 40, 35, 30, 25, or fewer hours after the administration of the dose. In some embodiments, the dose does not result in a toxic level of GAA in the liver of the individual.

In various non-limiting embodiments, the ASSC for the GAA enzyme is a small molecule inhibitor of the GAA enzyme, including reversible competitive inhibitors of the GAA enzyme.

In one embodiment the ASSC is represented by the formula:

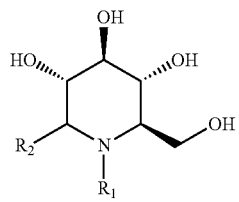

where $R_1$ is H or a straight or branched alkyl, cycloalkyl, alkoxyalkyl or aminoalkyl containing 1-12 carbon atoms optionally substituted with an —OH, —COOH, —Cl, —F, —CF$_3$, —OCF$_3$, —O—C(=O)N-(alkyl)$_2$; and $R_2$ is H or a straight or branched alkyl, cycloalkyl, or alkoxylalkyl containing 1-9 carbon atoms; including pharmaceutically acceptable salts, esters and prodrugs thereof. In one embodiment, the ASSC is as defined above, with $R_1$ being H. In another embodiment, the ASSC is as defined above, with $R_2$ being H.

In one particular non-limiting embodiment, the ASSC is 1-deoxynojirimycin (1-DNJ), which is represented by the following formula:

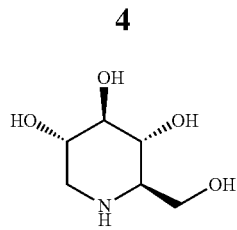

or a pharmaceutically acceptable salts, esters or prodrug of 1-deoxynojirimycin. In one embodiment, the salt is hydrochloride salt (i.e. 1-deoxynojirimycin-HCl).

In one particular non-limiting embodiment, the ASSC is N-butyl-deoxynojirimycin (NB-DNJ; Zavesca®, Actelion Pharmaceuticals Ltd, Switzerland), which is represented by the following formula:

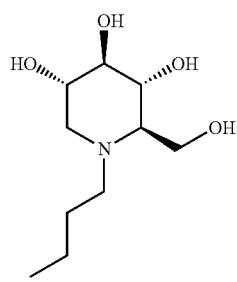

or a pharmaceutically acceptable salt, ester or prodrug of NB-DNJ.

In one particular non-limiting embodiment, the ASSC is $C_{10}H_{19}NO_4$, which is represented by the following formula:

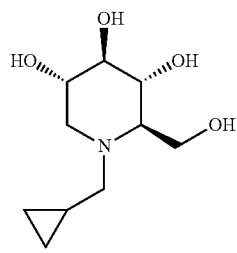 [SMILES: OC[C@@H]1[C@@H](O)[C@H](O)[C@@H](O)CN1CC1CC1]

or a pharmaceutically acceptable salt, ester or prodrug of $C_{10}H_{19}NO_4$. In one embodiment, the salt is hydrochloride salt.

In one particular non-limiting embodiment, the ASSC is $C_{12}H_{23}NO_4$, which is represented by the following formula:

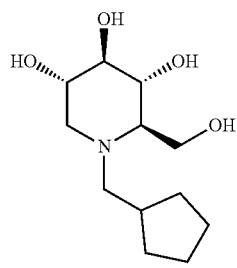 [SMILES: OC[C@@H]1[C@@H](O)[C@H](O)[C@@H](O)CN1CC1CCCC1]

or a pharmaceutically acceptable salt, ester or prodrug of $C_{12}H_{23}NO_4$. In one embodiment, the salt is hydrochloride salt.

4. BRIEF DESCRIPTION OF THE DRAWINGS

FIG. 1 depicts the stability of recombinant human GAA (Myozyme®, Genzyme Corp.) at ER pH (7.4) or lysosomal pH (5.2) in the presence or absence of 100 μM of 1-deoxynojirimycin hydrochloride (1-DNJ-HCl) as determined in a thermal stability assay. The thermal stability assay utilizes heat to induce protein denaturation, which is monitored using a SYPRO Orange dye that fluoresces upon binding to hydrophobic amino acids (which are not exposed in a folded protein). A protein structure that requires more heat to denature is by definition more stable. As shown above, Myozyme® is ordinarily much more stable at lysosomal pH (5.2) than at ER pH (7.4). However, the enzyme stability at pH 7.4 is significantly increased upon addition of 100 μM of 1-deoxynojirimycin, as compared to Myozyme® alone.

FIG. 2A depicts the effects of 1-DNJ-HCl on recombinant human GAA (Myozyme®, Genzyme Corp.) enzymatic activity at plasma pH (7.4) or lysosomal pH (5.2) at 37° C. GAA activity was evaluated to assess the ability of an ASSC of GAA to prolong the activity of the rhGAA over time. Myozyme® (45 nM) was incubated in pH 7.4 or pH 5.2 buffer with or without 50 μM 1-DNJ at 37° C. over 24 hours. Samples were assayed for GAA enzyme activity using 4-MU-α-glucose at 0, 3, 6 and 24 hours and the residual GAA activity was expressed as % of initial activity. These results indicate that 1-DNJ ameliorates the loss of GAA enzyme activity at plasma pH (7.4).

FIG. 2B depicts a parallel SYPRO Orange thermal stability experiment to determine if the loss of enzyme activity shown in FIG. 2A, particularly the loss of Myozyme® activity at ER pH (7.4), correlates with protein unfolding and denaturation. Myozyme® (0.9 μM) was incubated in pH 7.4 or pH 5.2 buffer with or without 100 μM 1-DNJ-HCl at 37° C. and the protein folding was monitored every hour over 24 hours. FIGS. 2A and 2B show that GAA denaturation correlates with loss of enzyme activity (compare curve with diamond curves in the two figures). More importantly, these results indicate that 1-DNJ can prevent GAA denaturation and loss of enzyme activity at plasma pH.

FIG. 3 depicts the results of GAA activity tests on GAA KO Mice Receiving ERT with and without concurrent oral administration of 1-DNJ-HCl. Myozyme® was administered via IV infusion at a dose of 10 mg/kg, once per week for up to 3 weeks either alone or in combination with 10, 100, or 1000 mg/kg of 1-DNJ-HCl 30 min prior to, and 8, 16, and 24 hours post-Myozyme® administration. These results demonstrate that Myozyme® tissue uptake (as a measure of GAA activity) declined at 7 days post injection. Coadministration of 1-DNJ-HCl with Myozyme® facilitated a dose-dependent increase in Myozyme® uptake for up to 7 days post injection. The effect of 1-DNJ-HCl was more pronounced and significant (p<0.05 t-test vs. Myozyme® alone) at 4 and 7 days post injection of either 1, 2, or 3 weekly infusions of Myozyme®.

FIG. 4 demonstrates that 1-DNJ-HCl inhibits GAA with an $IC_{50}$ of about 1 μM.

FIG. 5 depicts the results of a thermal stability assay that utilizes heat to induce protein denaturation, which is monitored using a SYPRO Orange dye that fluoresces upon binding to hydrophobic amino acids (which are not exposed in a folded protein). 1-DNJ-HCl increases GAA thermostability as evident by increases in GAA's melting temperature in a dose-dependent manner.

FIG. 6 depicts the results of GAA activity in rats over 24 hours after IV administration of 10 mg/kg of rhGAA or saline with and without 3 mg/kg or 30 mg/kg of orally administered 1-DNJ-HCl. The rhGAA or saline was administered 30 minutes after administration of the 1-DNJ-HCl. In this example, the 1-DNJ-HCl inhibited the loss of enzyme activity post-administration, thereby increasing the in vivo half life of rhGAA. The in vivo half life of rhGAA increased from 1.4±0.2 hours (0 mg/kg of 1-DNJ-HCl) to 2.1±0.2 hours (3 mg/kg of 1-DNJ-HCl) and 3.0±0.4 hours (30 mg/kg of 1-DNJ-HCl).

FIGS. 7A-7B depict the GAA activity in heart (A) and diaphragm tissue (B) for ERT monotherapy and ERT/ASSC co-therapy (rhGAA+1-DNJ-HCl) when administered to a GAA KO mouse. rhGAA uptake in the heart and diaphragm is increased when co-administered with 1-DNJ-HCl.

FIG. 8 shows that 1-DNJ-HCl prevents rhGAA enzyme inactivation in blood. Myozyme® (0.5 μM) was incubated at 37° C. in citrate anti-coagulated whole blood in the presence or absence of 50 μM 1-DNJ-HCl. Aliquots were collected at 0, 2, 4, 8 and 24 hrs and centrifuged to obtain plasma. These plasma samples were then diluted in potassium acetate buffer (pH 4.0) and assayed for GAA activity using the 4-methylumbeliferyl-α-glucose (4-MUG) fluorogenic substrate. The measured GAA activity for individual samples at each time point was normalized to the 0 hr and expressed as % of initial activity. Data from 4 independent experiments were analyzed to obtain the mean (and standard deviation) and plotted versus time to assess the loss of enzyme activity over this time course.

FIG. 9 shows that low 1-DNJ-HCl concentrations prevent rhGAA enzyme inactivation in blood. Myozyme® (0.5 μM) was incubated at 37° C. in citrate anti-coagulated whole blood with varying 1-DNJ-HCl concentrations (0-100 μM). Aliquots were collected at 0, 3 and 6 hrs and centrifuged to obtain plasma. These plasma samples were then diluted in potassium acetate buffer (pH 4.0) and assayed for GAA activity using the 4-methylumbeliferyl-α-glucose (4-MUG) fluorogenic substrate. The measured GAA activity for individual samples at each time point was normalized to the 0 hr and expressed as % of initial activity. The residual GAA enzyme activity was plotted versus time to assess the loss of enzyme activity with respect to 1-DNJ-HCl concentration over this time course.

FIG. 10 shows the experimental design for Example 9.

FIGS. 11A-11D show that Myozyme® co-administered with 1-DNJ-HCl resulted in significantly greater tissue glycogen reduction in GAA KO mice as compared to Myozyme® alone. Glycogen reduction with Myozyme® alone was 93±1%, 41±4%, 69±3%, and 18±4%, in heart (A), diaphragm (B), soleus (C), and quadriceps (D), respectively, relative to untreated mice. Glycogen reduction with Myozyme® co-administered with 1-DNJ-HCl was 96±0.6%, 66±5%, 82±3%, and 23±3%, respectively.

FIG. 12 shows that combining 1 mM DNJ with 25 mg/mL Myozyme® reduces aggregation of Myozyme® at neutral pH 7.4 and 37° C. Aggregation was assessed after a 4 week incubation period.

Figure 16A:
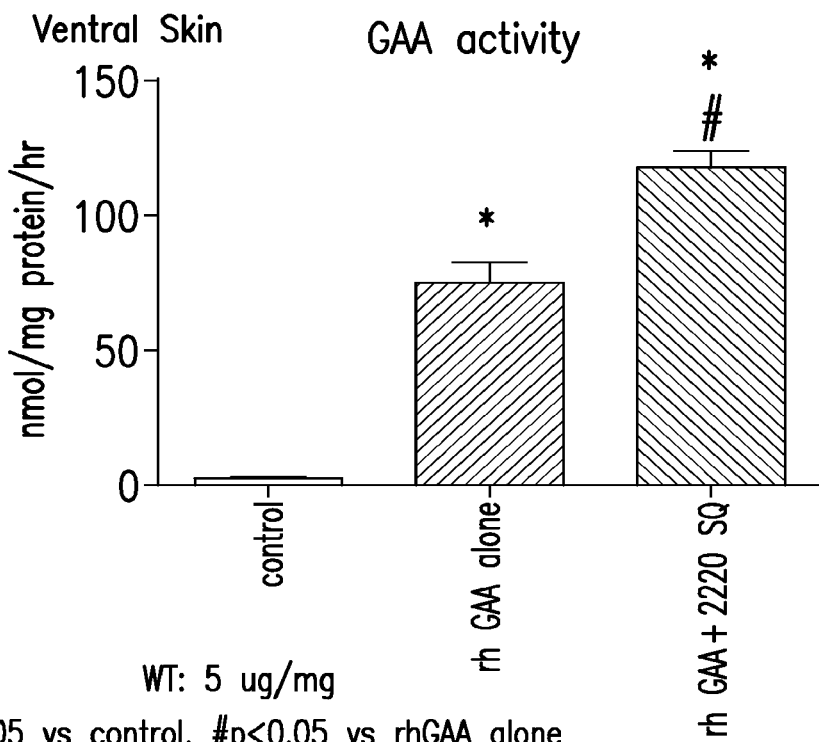
Figure 16B:
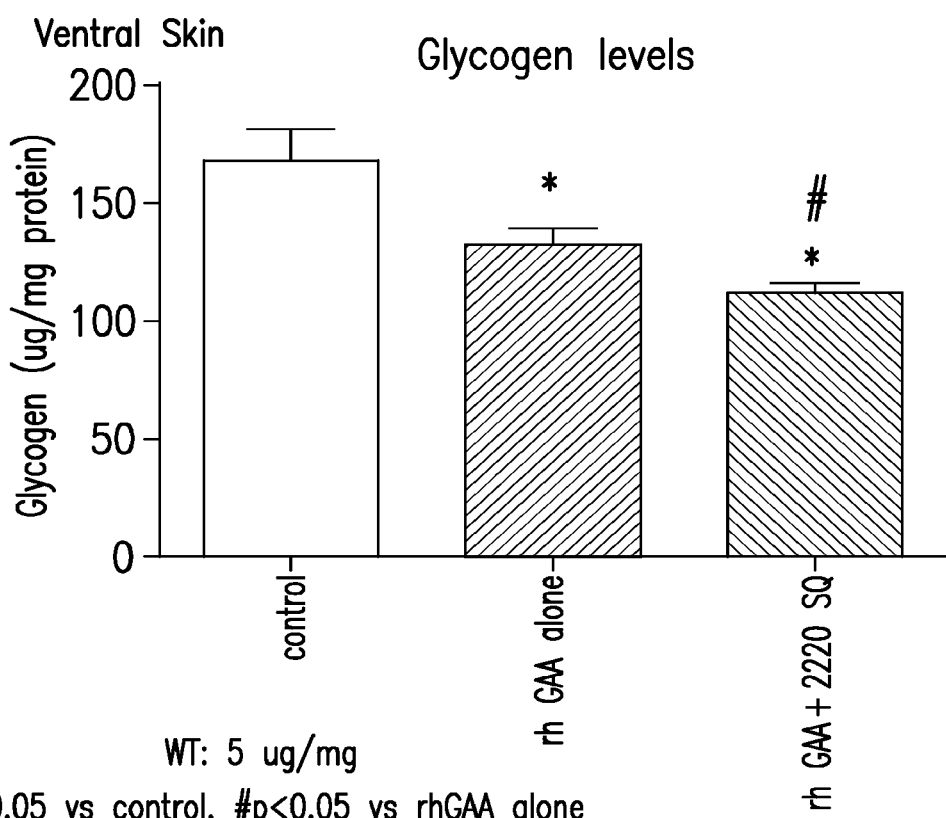

FIGS. 16A-16B show rhGAA activity (A) and glycogen level (B) in ventral skin 3 days (A) and 14 days (B) following the last subcutaneous administration of rhGAA or a co-formulation of rhGAA and 1-DNJ to mouse, as described in Example 13.

Figure 17A:
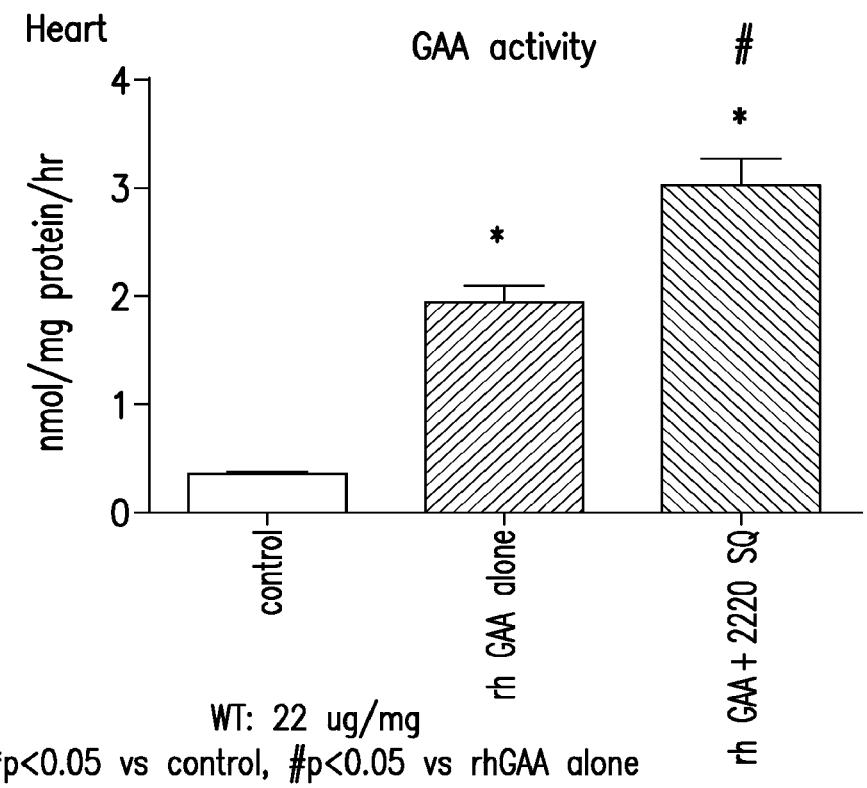
Figure 17B:
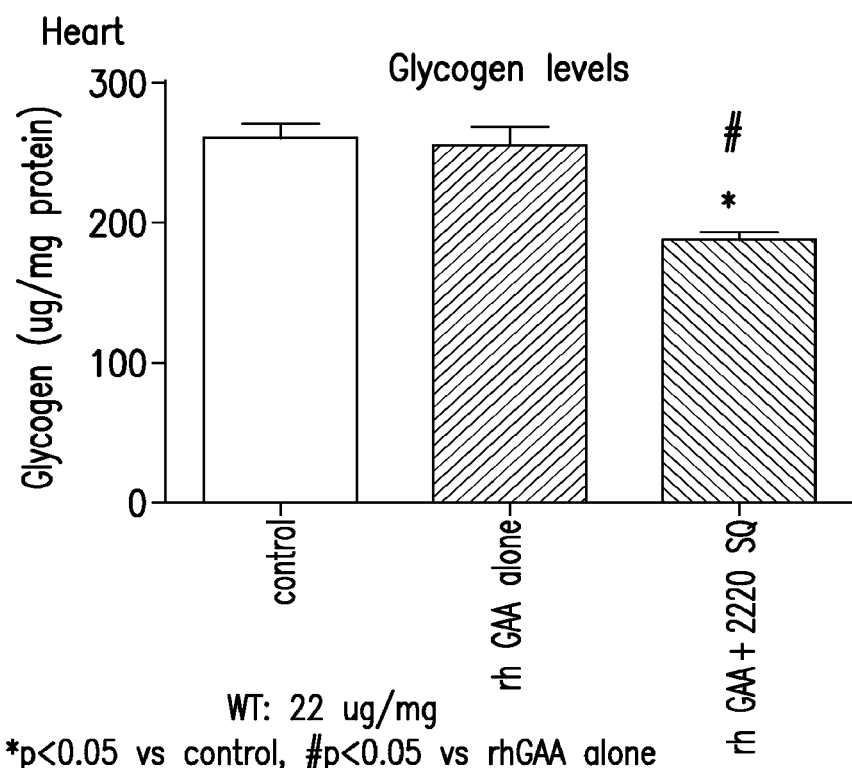

FIGS. 17A-17B show rhGAA activity (A) and glycogen level (B) in heart 3 days (A) and 14 days (B) following the last subcutaneous administration of rhGAA or a co-formulation of rhGAA and 1-DNJ to mouse, as described in Example 13.

Figure 18A:
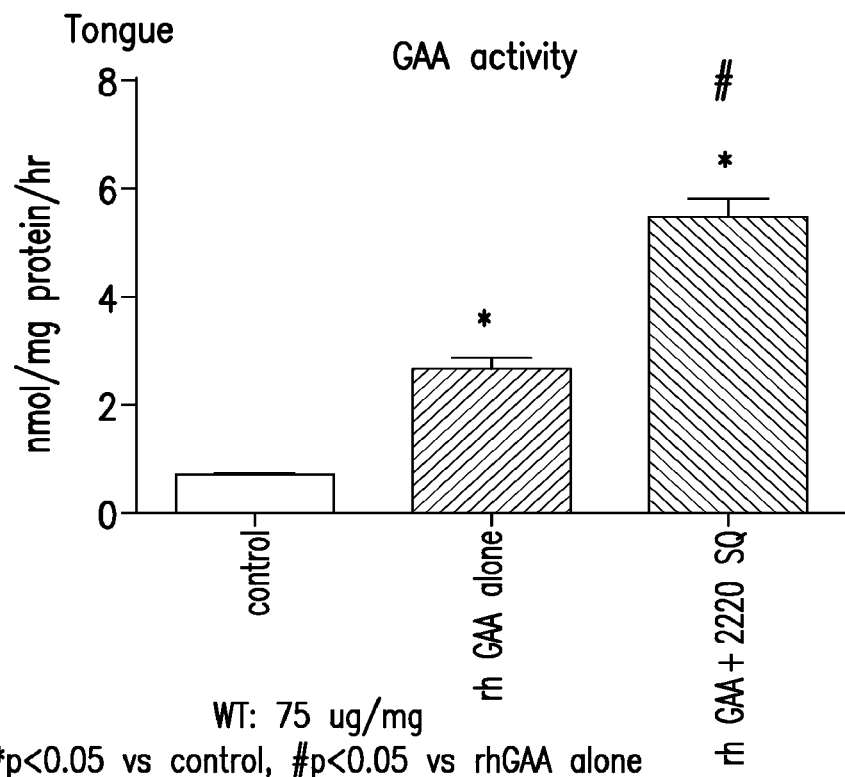
Figure 18B:
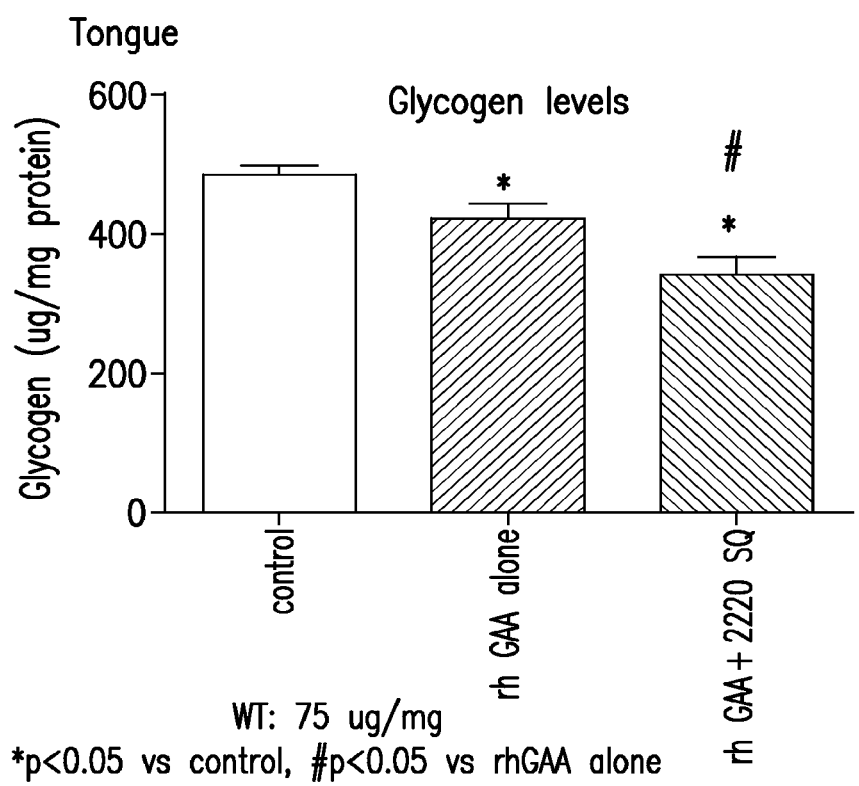

FIGS. 18A-18B show rhGAA activity (A) and glycogen level (B) in tongue 3 days (A) and 14 days (B) following the last subcutaneous administration of rhGAA or a co-formulation of rhGAA and 1-DNJ to mouse, as described in Example 13.

Figure 19A:
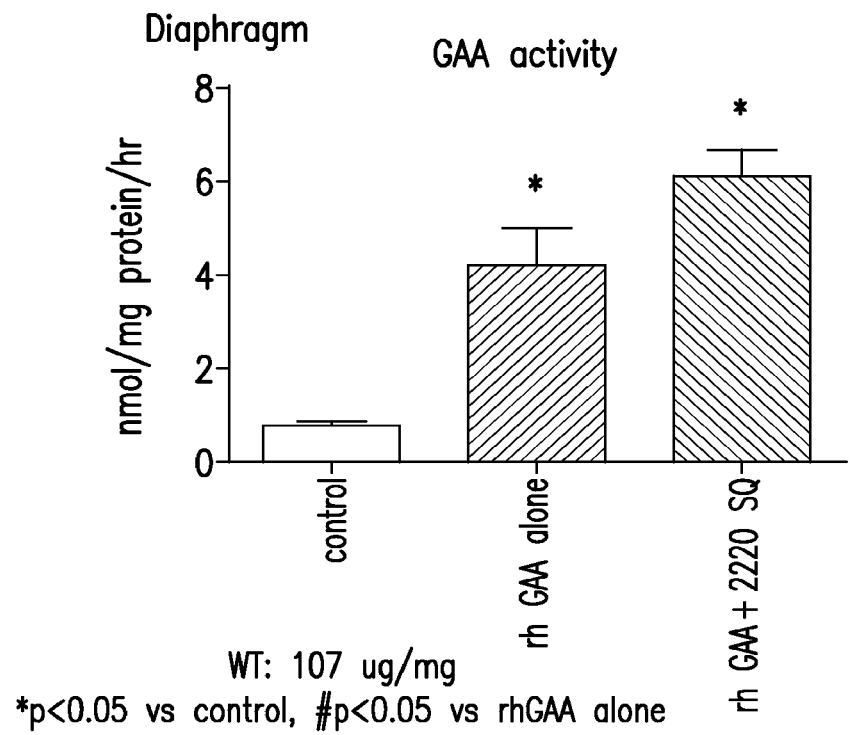
Figure 19B:
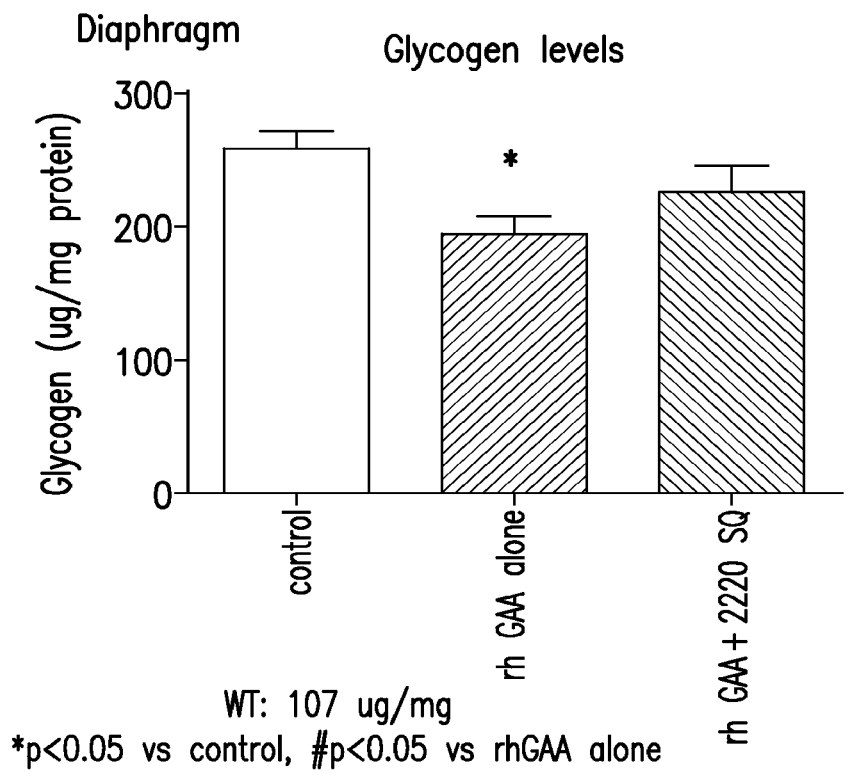

FIGS. 19A-19B show rhGAA activity (A) and glycogen level (B) in diaphragm 3 days (A) and 14 days (B) following the last subcutaneous administration of rhGAA or a co-formulation of rhGAA and 1-DNJ to mouse, as described in Example 13.

Figure 20A:
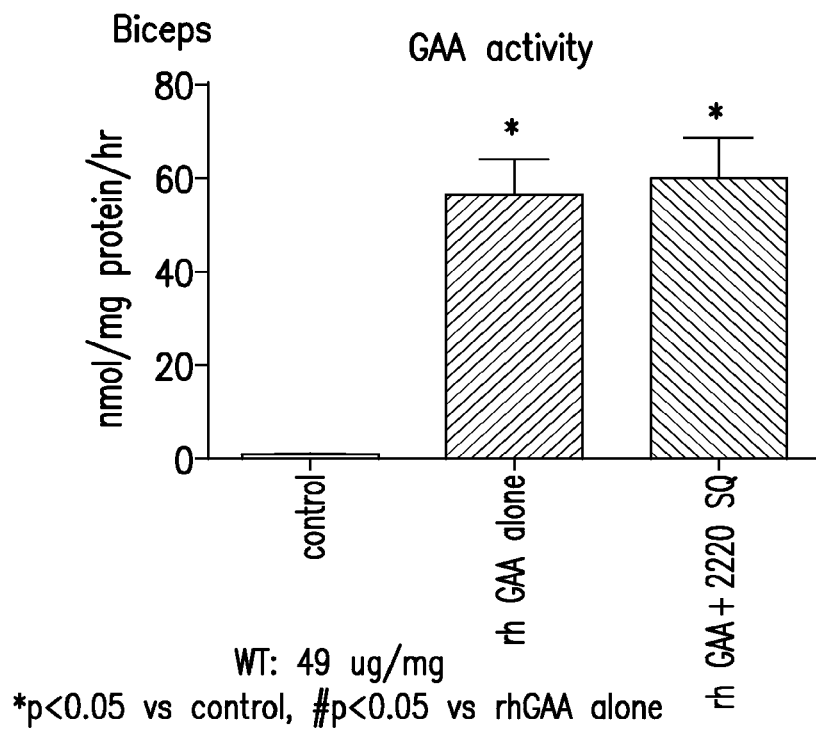
Figure 20B:
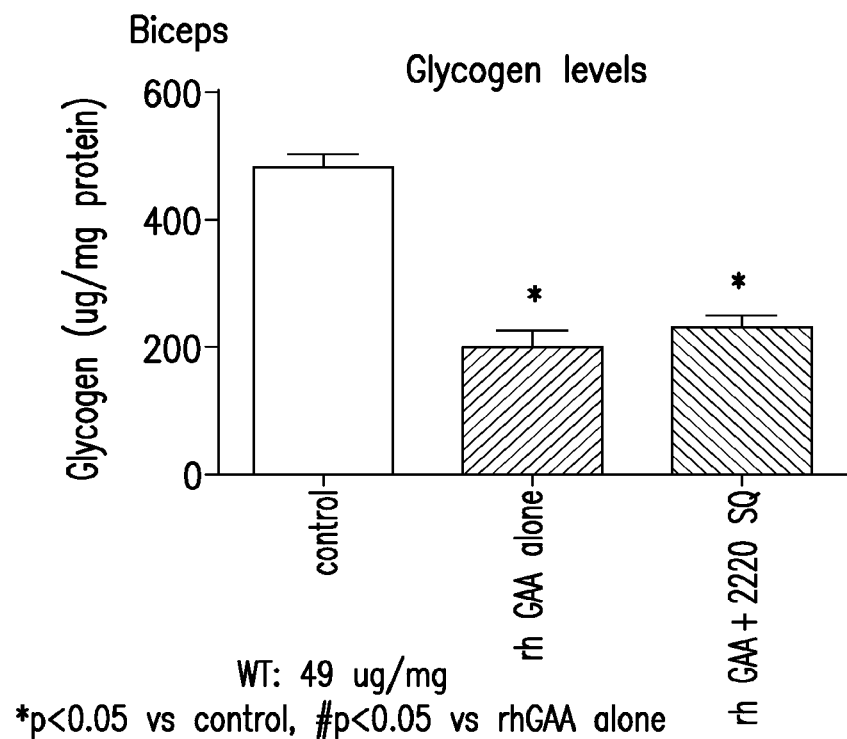

FIGS. 20A-20B show rhGAA activity (A) and glycogen level (B) in biceps 3 days (A) and 14 days (B) following the last subcutaneous administration of rhGAA or a co-formulation of rhGAA and 1-DNJ to mouse, as described in Example 13.

Figure 21A:
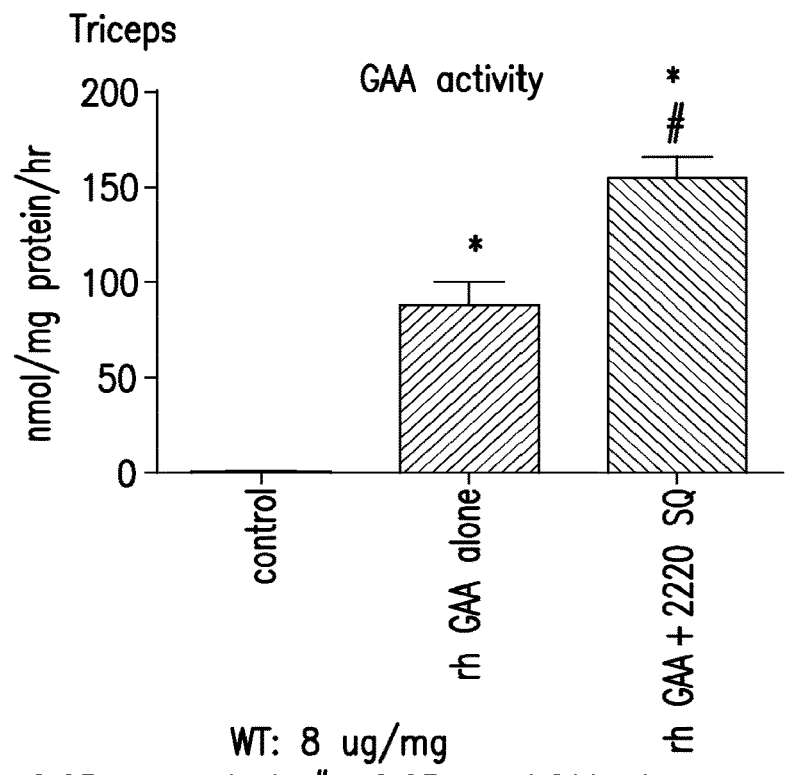
Figure 21B:
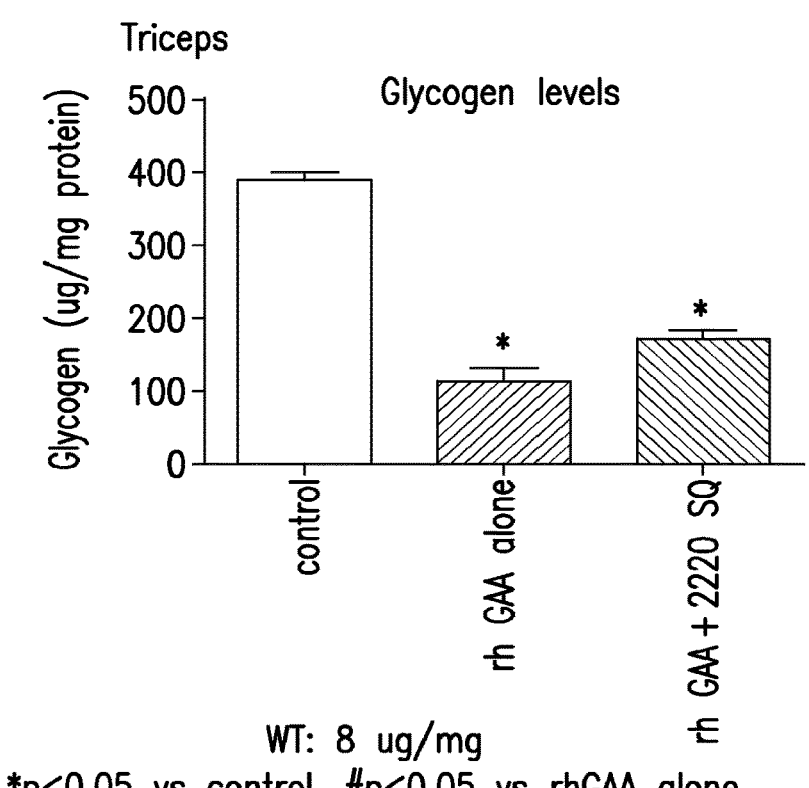

FIGS. 21A-21B show rhGAA activity (A) and glycogen level (B) in triceps 3 days (A) and 14 days (B) following the last subcutaneous administration of rhGAA or a co-formulation of rhGAA and 1-DNJ to mouse, as described in Example 13.

Figure 22A:
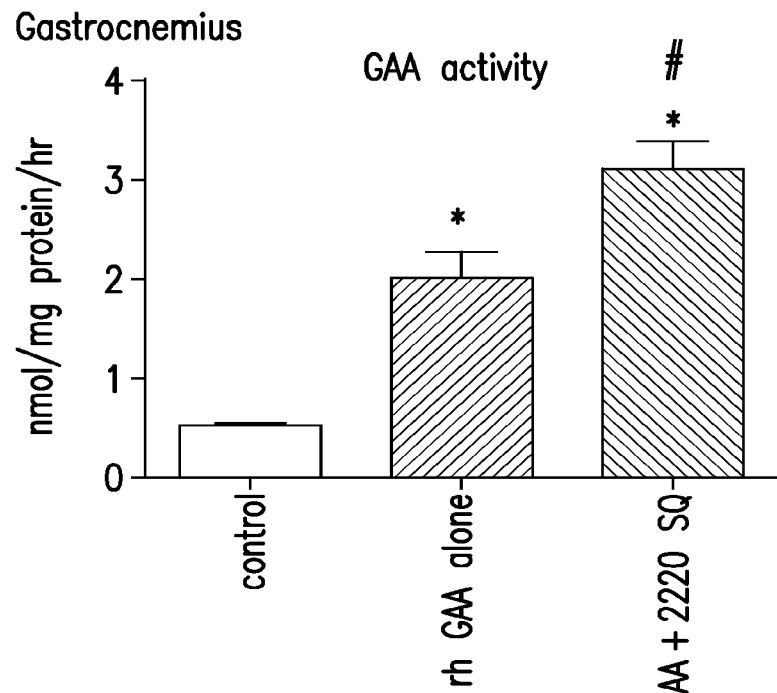
Figure 22B:
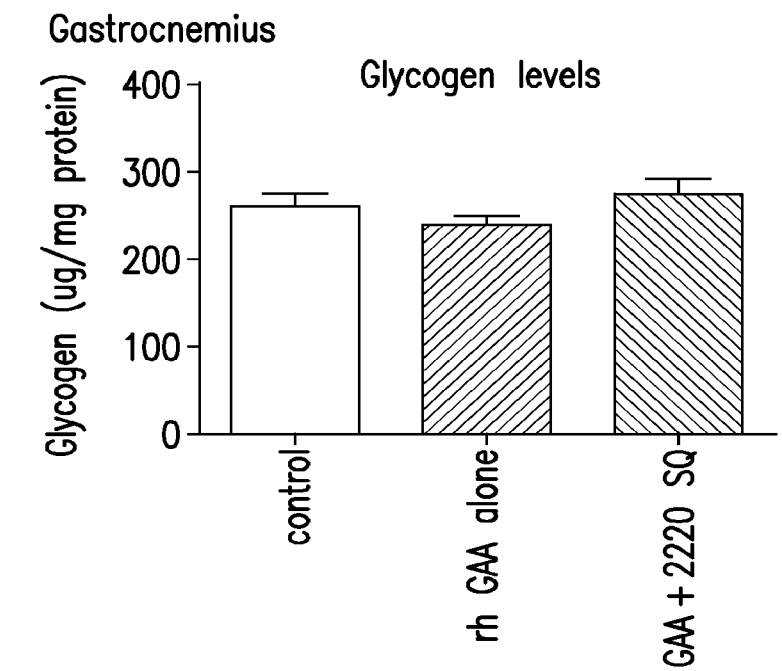

FIGS. 22A-22B show rhGAA activity (A) and glycogen level (B) in gastrocnemius 3 days (A) and 14 days (B) following the last subcutaneous administration of rhGAA or a co-formulation of rhGAA and 1-DNJ to mouse, as described in Example 13.

Figure 23A:
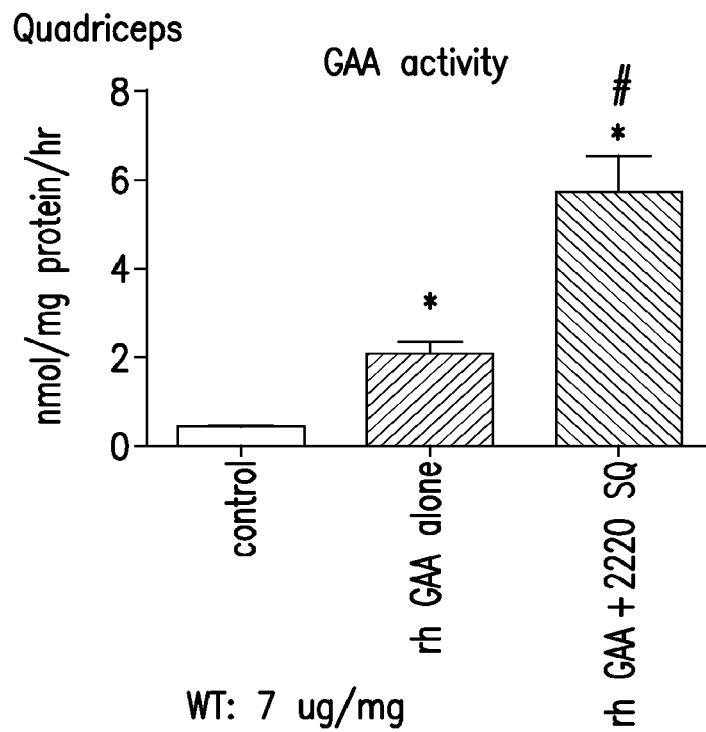
Figure 23B:
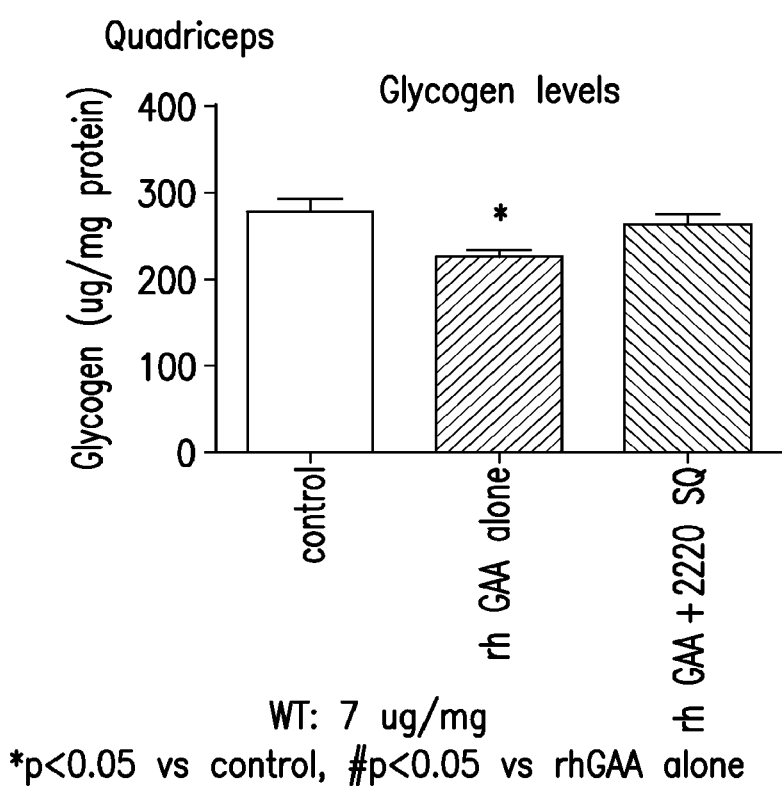

FIGS. 23A-23B show rhGAA activity (A) and glycogen level (B) in quadriceps 3 days (A) and 14 days (B) following the last subcutaneous administration of rhGAA or a co-formulation of rhGAA and 1-DNJ to mouse, as described in Example 13.

Figure 24:
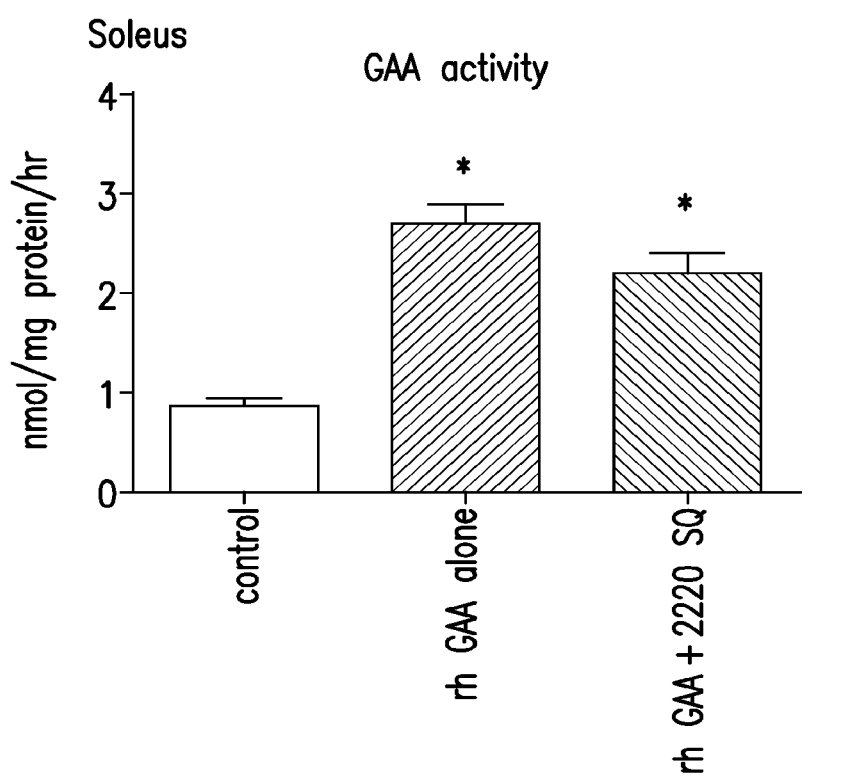

FIG. 24 shows rhGAA activity in soleus 3 days following the last subcutaneous administration of rhGAA or a co-formulation of rhGAA and 1-DNJ to mouse, as described in Example 13.

Figure 25:
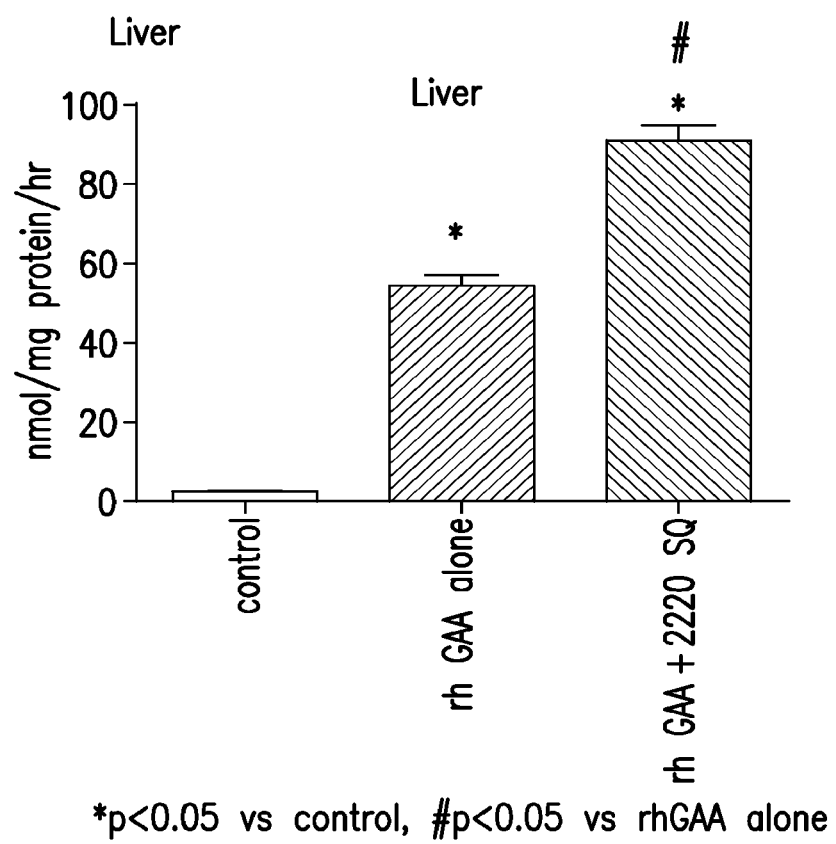

FIG. 25 shows rhGAA activity in liver 3 days following the last subcutaneous administration of rhGAA or a co-formulation of rhGAA and 1-DNJ to mouse, as described in Example 13.

Figure 26:
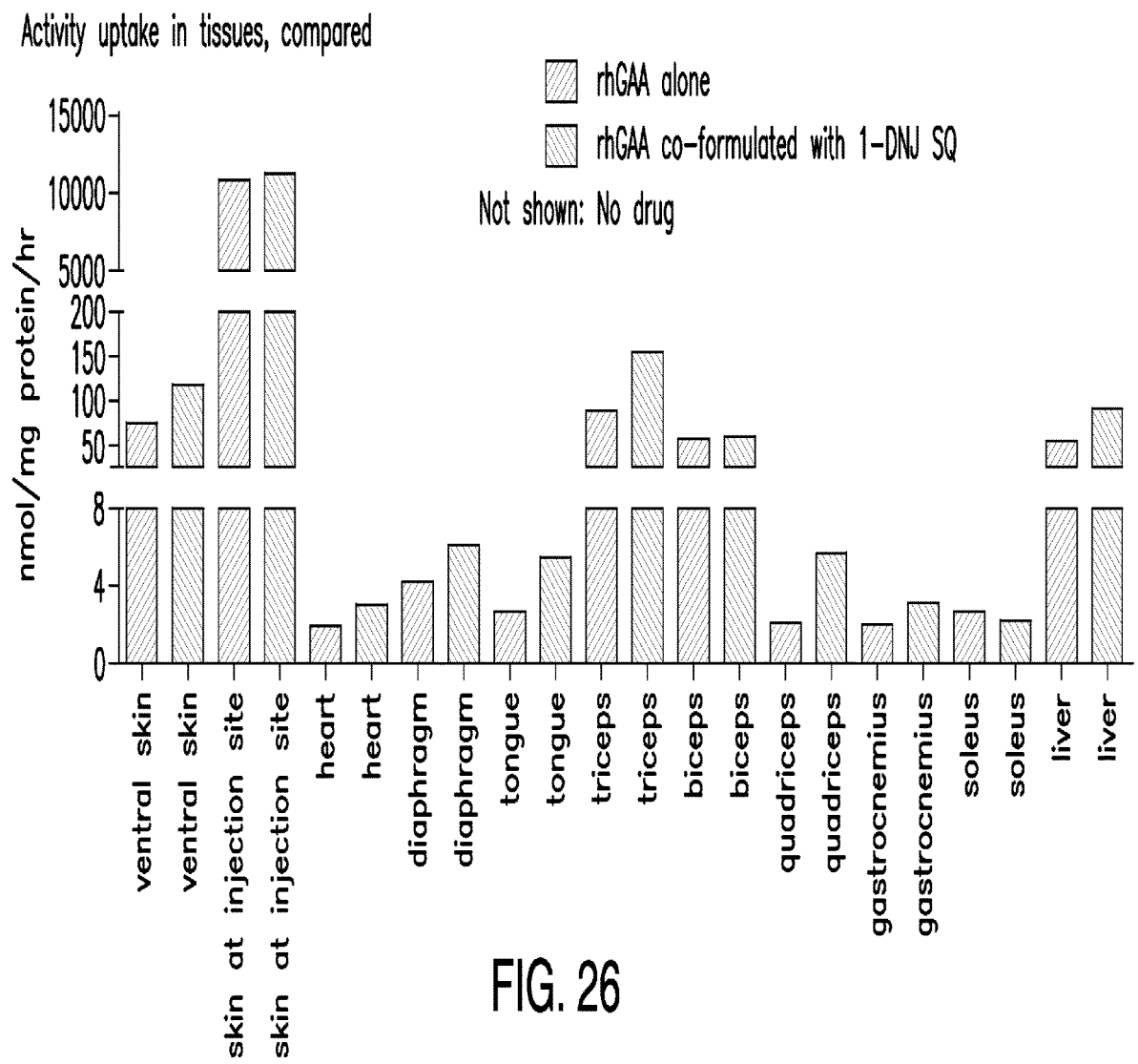

FIG. 26 shows a comparison of rhGAA activity in the various tissues tested 3 days following the last subcutaneous administration of rhGAA or a co-formulation of rhGAA and 1-DNJ to mouse, as described in Example 13.

Figure 27A:
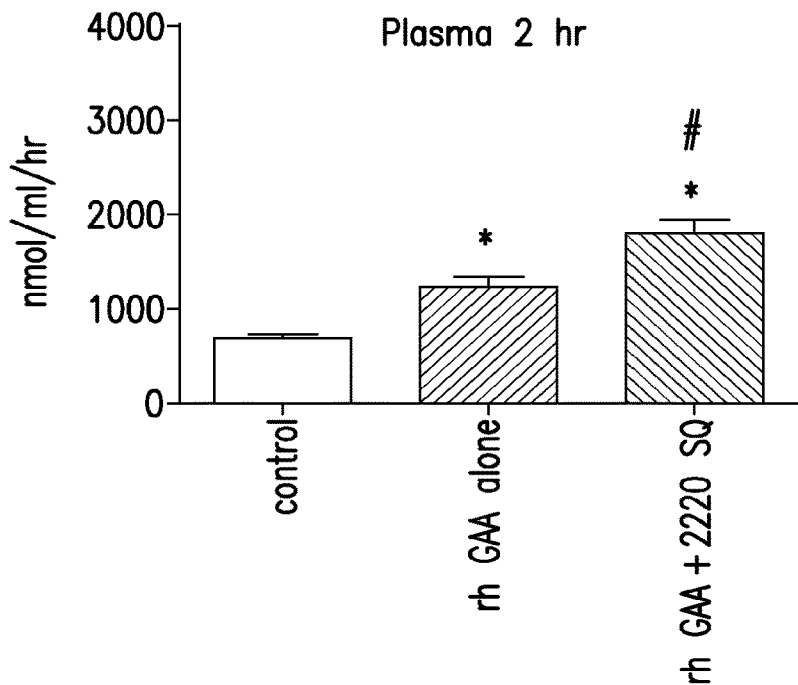
Figure 27B:
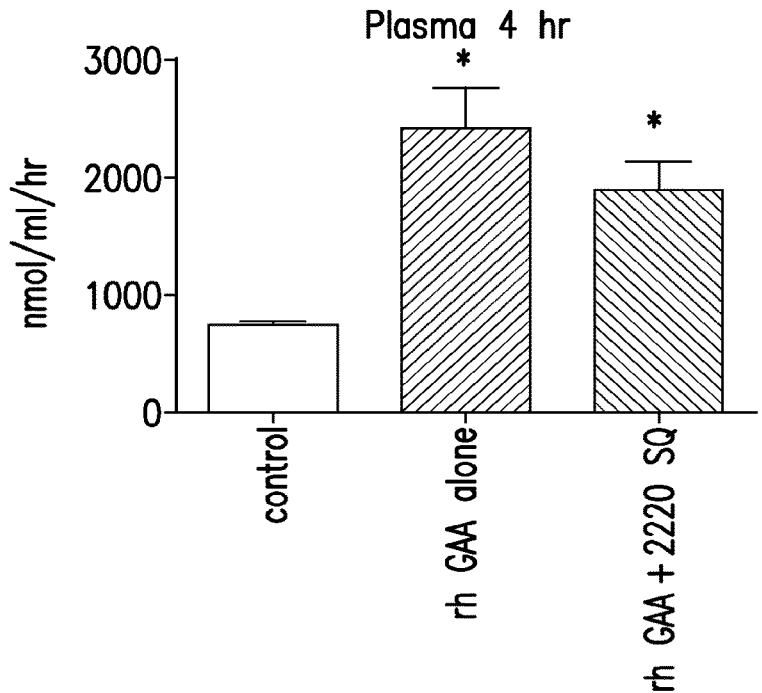

FIGS. 27A-27B show plasma rhGAA activity 2 hours (A) and 4 hours (B) following the last subcutaneous administration of rhGAA or a co-formulation of rhGAA and 1-DNJ to mouse, as described in Example 13.

Figure 28A:
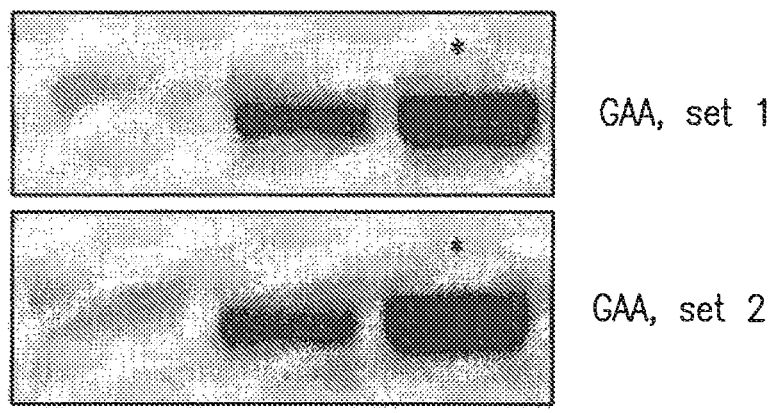
Figure 28B:
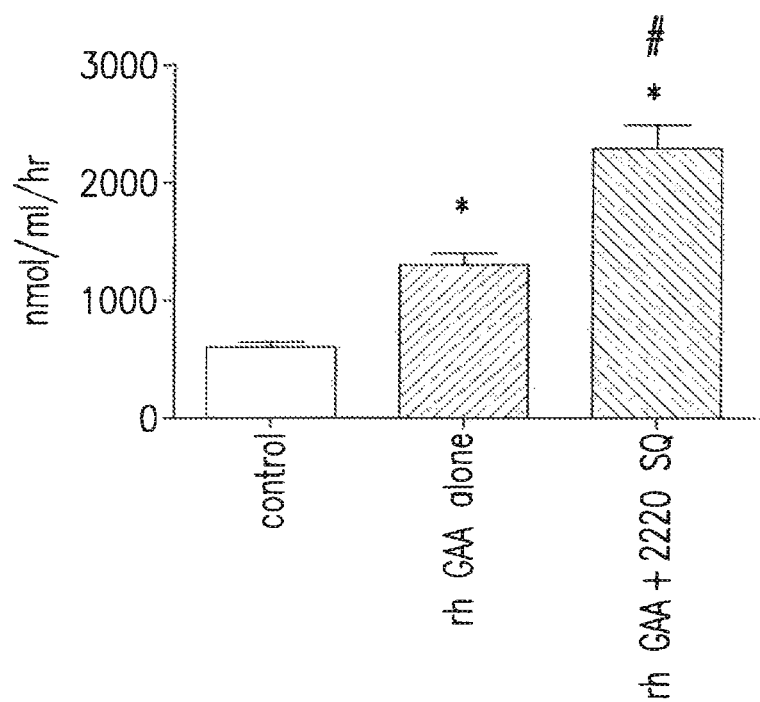

FIGS. 28A-28B show plasma rhGAA activity (B) and plasma GAA protein level (as measured by Western blot) (A) 2 hours following the last subcutaneous administration of rhGAA or a co-formulation of rhGAA and 1-DNJ to mouse, as described in Example 13.

Figure 29A:
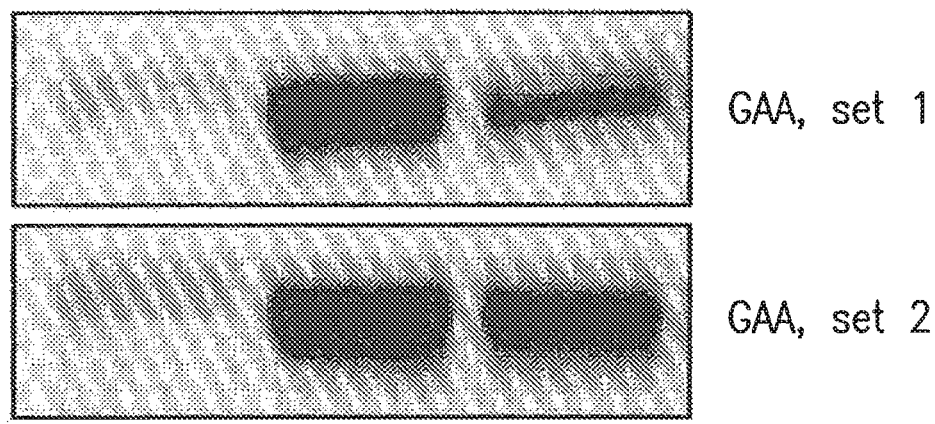
Figure 29B:
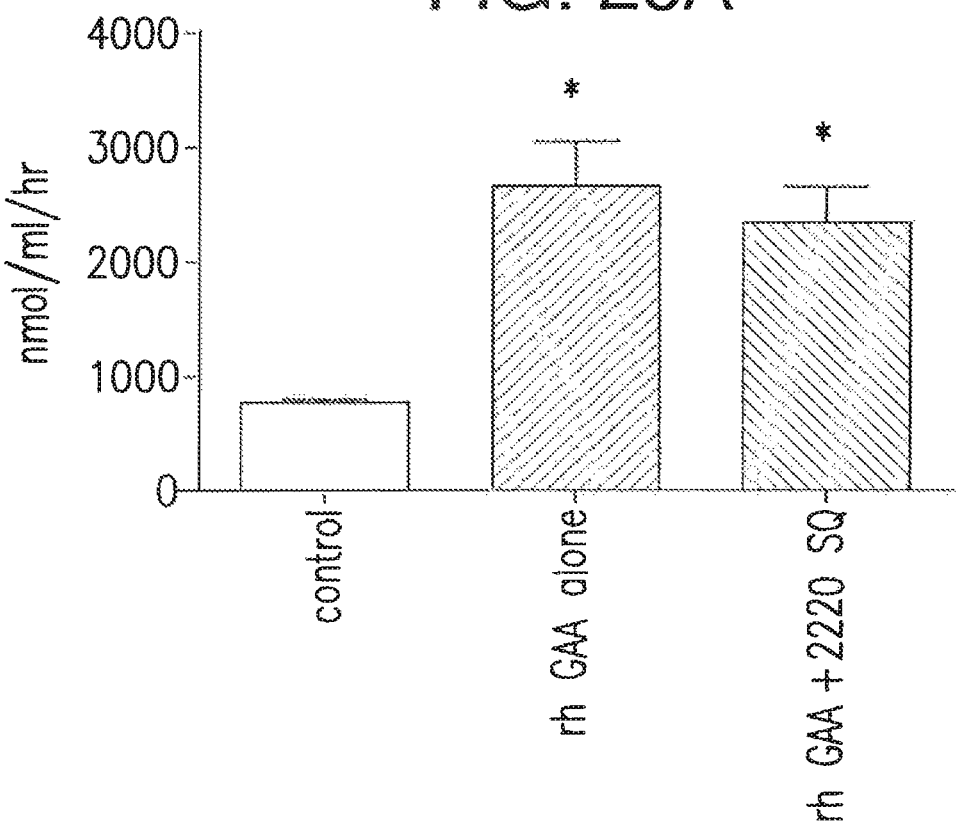

FIGS. 29A-29B show plasma rhGAA activity (B) and plasma GAA protein level (as measured by Western blot) (A) 4 hours following the last subcutaneous administration of rhGAA or a co-formulation of rhGAA and 1-DNJ to mouse, as described in Example 13.

5. DETAILED DESCRIPTION

The present invention is based at least in part on the discovery that combining an acid α-glucosidase (GAA) enzyme (e.g., a recombinant human GAA (rhGAA)), with an ASSC for the GAA enzyme (e.g., 1-deoxynojirimycin), results in a surprising increase in GAA activity in vivo as compared to either treatment alone. The present invention is also based at least in part on the discovery that a GAA enzyme (e.g., rhGAA) stabilizes a proper conformation—both in vitro and in vivo—upon addition of an ASSC for the GAA enzyme. The present invention is also based at least in part on the discovery that combining an ASSC with a high concentration of GAA reduces GAA aggregation, which commonly occurs with increased GAA concentration.

For clarity and not by way of limitation, this detailed description is divided into the following sub-portions:
(i) Definitions;
(ii) Pompe Disease;
(iii) Obtaining GAA and ASSC;
(iv) Treatment of Pompe Disease with ERT and an ASSC;
(v) Pharmaceutical Compositions;
(vi) In Vitro Stability; and
(vii) In Vivo Stability.

5.1 Definitions

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

According to the invention, a "subject" or "patient" is a human or non-human animal. Although the animal subject is preferably a human, the compounds and compositions of the invention have application in veterinary medicine as well, e.g., for the treatment of domesticated species such as canine, feline, and various other pets; farm animal species such as bovine, equine, ovine, caprine, porcine, etc.; wild animals, e.g., in the wild or in a zoological garden; and avian species, such as chickens, turkeys, quail, songbirds, etc.

The term "enzyme replacement therapy" or "ERT" refers to refers to the introduction of a non-native, purified enzyme into an individual having a deficiency in such enzyme. The administered enzyme can be obtained from natural sources or by recombinant expression. The term also refers to the introduction of a purified enzyme in an individual otherwise requiring or benefiting from administration of a purified enzyme, e.g., suffering from protein insufficiency. The introduced enzyme may be a purified, recombinant enzyme produced in vitro, or enzyme purified from isolated tissue or fluid, such as, e.g., placenta or animal milk, or from plants.

The term "stabilize a proper conformation" refers to the ability of a compound or peptide or other molecule to associate with a wild-type protein, or to a mutant protein that can perform its wild-type function in vitro and in vivo, in such a way that the structure of the wild-type or mutant protein can be maintained as its native or proper form. This effect may manifest itself practically through one or more of (i) increased shelf-life of the protein; (ii) higher activity per unit/amount of protein; or (iii) greater in vivo efficacy. It may be observed experimentally through increased yield from the ER during expression; greater resistance to unfolding due to temperature increases (e.g., as determined in thermal stability assays), or the present of chaotropic agents, and by similar means.

As used herein, the term "active site" refers to the region of a protein that has some specific biological activity. For example, it can be a site that binds a substrate or other binding partner and contributes the amino acid residues that directly participate in the making and breaking of chemical bonds. Active sites in this invention can encompass catalytic sites of enzymes, antigen biding sites of antibodies, ligand binding domains of receptors, binding domains of regulators, or receptor binding domains of secreted proteins. The active sites can also encompass transactivation, protein-protein interaction, or DNA binding domains of transcription factors and regulators.

As used herein, the term "active site-specific chaperone" refers to any molecule including a protein, peptide, nucleic acid, carbohydrate, etc. that specifically interacts reversibly with an active site of a protein and enhances formation of a stable molecular conformation. As used herein, "active site-specific chaperone" does not include endogenous general chaperones present in the ER of cells such as Bip, calnexin or calreticulin, or general, non-specific chemical chaperones such as deuterated water, DMSO, or TMAO.

The term "purified" as used herein refers to material that has been isolated under conditions that reduce or eliminate the presence of unrelated materials, i.e., contaminants, including native materials from which the material is obtained. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 95% pure; more preferably, at least 97% pure, and more preferably still at least 99% pure. Purity can be evaluated by chromatography, gel electrophoresis, immunoassay, composition analysis, biological assay, and other methods known in the art. In a specific embodiment, purified means that the level of contaminants is below a level acceptable to regulatory authorities for safe administration to a human or non-human animal.

As used herein, the terms "mutant" and "mutation" mean any detectable change in genetic material, e.g., DNA, or any process, mechanism or result of such a change. This includes gene mutations, in which the structure (e.g., DNA sequence) of a gene is altered, any gene or DNA arising from any mutation process, and any expression product (e.g., RNA, protein or enzyme) expressed by a modified gene or DNA sequence.

As used herein the term "mutant protein" refers to proteins translated from genes containing genetic mutations that result in altered protein sequences. In a specific embodiment, such mutations result in the inability of the protein to achieve its native conformation under the conditions normally present in the ER. The failure to achieve this conformation results in these proteins being degraded, rather than being transported through their normal pathway in the protein transport system to their proper location within the cell. Other mutations can result in decreased activity or more rapid turnover.

As used herein the term "wild-type gene" refers to a nucleic acid sequences which encodes a protein capable of having normal biological functional activity in vivo. The wild-type nucleic acid sequence may contain nucleotide changes that differ from the known, published sequence, as long as the changes result in amino acid substitutions having little or no effect on the biological activity. The term wild-type may also include nucleic acid sequences engineered to encode a protein capable of increased or enhanced activity relative to the endogenous or native protein.

As used herein, the term "wild-type protein" refers to any protein encoded by a wild-type gene that is capable of having functional biological activity when expressed or introduced in vivo. The term "normal wild-type activity" refers to the normal physiological function of a protein in a cell. Such functionality can be tested by any means known to establish functionality of a protein.

The term "genetically modified" refers to cells that express a particular gene product following introduction of a nucleic acid comprising a coding sequence which encodes the gene product, along with regulatory elements that control expression of the coding sequence. Introduction of the nucleic acid may be accomplished by any method known in the art including gene targeting and homologous recombination. As used herein, the term also includes cells that have been engineered to express or overexpress an endogenous gene or gene product not normally expressed by such cell, e.g., by gene activation technology.

The phrase "pharmaceutically acceptable", whether used in connection with the pharmaceutical compositions of the invention, refers to molecular entities and compositions that are physiologically tolerable and do not typically produce untoward reactions when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition.

The terms "therapeutically effective dose" and "effective amount" refer to the amount of the compound that is sufficient to result in a therapeutic response. In embodiments where an ASSC and GAA are administered in a complex, the terms "therapeutically effective dose" and "effective amount" may refer to the amount of the complex that is sufficient to result in a therapeutic response. A therapeutic response may be any response that a user (e.g., a clinician) will recognize as an effective response to the therapy. Thus, a therapeutic response will generally be an amelioration of one or more symptoms or sign of a disease or disorder.

It should be noted that a concentration of the ASSC that is inhibitory during in vitro production, transportation, or storage of the purified therapeutic protein may still constitute an "effective amount" for purposes of this invention because of dilution (and consequent shift in binding due to the change in equilibrium), bioavailability and metabolism of the ASSC upon administration in vivo.

The term 'alkyl' refers to a straight or branched hydrocarbon group consisting solely of carbon and hydrogen atoms, containing no unsaturation, and which is attached to the rest of the molecule by a single bond, e.g., methyl, ethyl, n-propyl, 1-methylethyl (isopropyl), n-butyl, n-pentyl, 1,1-dimethylethyl (t-butyl).

The term "alkenyl" refers to a $C_2$-$C_{20}$ aliphatic hydrocarbon group containing at least one carbon-carbon double bond and which may be a straight or branched chain, e.g., ethenyl, 1-propenyl, 2-propenyl (allyl), iso-propenyl, 2-methyl-1-propenyl, 1-butenyl, 2-butenyl.

The term "cycloalkyl" denotes an unsaturated, non-aromatic mono- or multicyclic hydrocarbon ring system such as cyclopropyl, cyclobutyl, cyclopentyl, cyclohexyl. Examples of multicyclic cycloalkyl groups include perhydronaphthyl, adamantyl and norbornyl groups bridged cyclic group or sprirobicyclic groups, e.g., spiro (4,4) non-2-yl.

The term "aryl" refers to aromatic radicals having in the range of about 6 to about 14 carbon atoms such as phenyl, naphthyl, tetrahydronapthyl, indanyl, biphenyl.

The term "heterocyclic" refers to a stable 3- to 15-membered ring radical which consists of carbon atoms and from one to five heteroatoms selected from the group consisting of nitrogen, oxygen and sulfur. For purposes of this invention, the heterocyclic ring radical may be a monocyclic or bicyclic ring system, which may include fused or bridged ring systems, and the nitrogen, carbon, oxygen or sulfur atoms in the heterocyclic ring radical may be optionally oxidized to various oxidation states. In addition, a nitrogen atom, where present, may be optionally quaternized; and the ring radical may be partially or fully saturated (i.e., heteroaromatic or heteroaryl aromatic).

The heterocyclic ring radical may be attached to the main structure at any heteroatom or carbon atom that results in the creation of a stable structure.

The term "heteroaryl" refers to a heterocyclic ring wherein the ring is aromatic.

The substituents in the 'substituted alkyl', 'substituted alkenyl', 'substituted cycloalkyl', 'substituted aryl' and 'substituted heteroaryl' may be the same or different, with one or more selected from the groups hydrogen, halogen, acetyl, nitro, carboxyl, oxo (=O), $CF_3$, —$OCF_3$, $NH_2$, —C(=O)-alkyl$_2$, $OCH_3$, or optionally substituted groups selected from alkyl, alkoxy and aryl.

The term "halogen" refers to radicals of fluorine, chlorine, bromine and iodine.

5.2 Pompe Disease

Pompe disease is an autosomal recessive LSD characterized by deficient acid alpha glucosidase (GAA) activity which impairs lysosomal glycogen metabolism. The enzyme deficiency leads to lysosomal glycogen accumulation and results in progressive skeletal muscle weakness, reduced cardiac function, respiratory insufficiency, and/or CNS impairment at late stages of disease. Genetic mutations in the GAA gene result in either lower expression or produce mutant forms of the enzyme with altered stability, and/or biological activity ultimately leading to disease. (see generally Hirschhorn R, 1995, Glycogen Storage Disease Type II: Acid α-Glucosidase (Acid Maltase) Deficiency, The Metabolic and Molecular Bases of Inherited Disease, Scriver et al., eds., McGraw-Hill, New York, 7th ed., pages 2443-2464). The three recognized clinical forms of Pompe disease (infantile, juvenile and adult) are correlated with the level of residual α-glucosidase activity (Reuser A J et al., 1995, Glycogenosis Type II (Acid Maltase Deficiency), Muscle & Nerve Supplement 3, S61-S69). ASSC (also referred to elsewhere as "pharmacological chaperones") represent a promising new therapeutic approach for the treatment of genetic diseases, such as lysosomal storage disorders (e.g., Pompe Disease).

Infantile Pompe disease (type I or A) is most common and most severe, characterized by failure to thrive, generalized hypotonia, cardiac hypertrophy, and cardiorespiratory failure within the second year of life. Juvenile Pompe disease (type II or B) is intermediate in severity and is characterized by a predominance of muscular symptoms without cardiomegaly. Juvenile Pompe individuals usually die before reaching 20 years of age due to respiratory failure. Adult Pompe disease (type III or C) often presents as a slowly progressive myopathy in the teenage years or as late as the sixth decade (Felice K J et al., 1995, Clinical Variability in Adult-Onset Acid Maltase Deficiency: Report of Affected Sibs and Review of the Literature, Medicine 74, 131-135).

In Pompe, it has been shown that α-glucosidase is extensively modified post-translationally by glycosylation, phosphorylation, and proteolytic processing. Conversion of the 110 kilodalton (kDa) precursor to 76 and 70 kDa mature forms by proteolysis in the lysosome is required for optimum glycogen catalysis.

As used herein, the term "Pompe Disease" refers to all types of Pompe Disease. The formulations and dosing regimens disclosed in this application may be used to treat, for example, Type I, Type II or Type III Pompe Disease.

5.3 Obtaining GAA and ASSC

GAA may be obtained from a cell endogenously expressing the GAA, or the GAA may be a recombinant human GAA (rhGAA), as described herein. In one, non-limiting embodiment, the rhGAA is a full length wild-type GAA. In other non-limiting embodiments, the rhGAA comprises a subset of the amino acid residues present in a wild-type GAA, wherein the subset includes the amino acid residues of the wild-type GAA that form the active site for substrate binding and/or substrate reduction. As such, the present invention contemplates an rhGAA that is a fusion protein comprising the wild-type GAA active site for substrate binding and/or substrate reduction, as well as other amino acid residues that may or may not be present in the wild type GAA.

GAA may be obtained from commercial sources or may be obtained by synthesis techniques known to a person of ordinary skill in the art. The wild-type enzyme can be purified from a recombinant cellular expression system (e.g., mammalian cells or insect cells-see generally U.S. Pat. No. 5,580,757 to Desnick et al.; U.S. Pat. Nos. 6,395,884 and 6,458,574 to Selden et al.; U.S. Pat. No. 6,461,609 to Calhoun et al.; U.S. Pat. No. 6,210,666 to Miyamura et al.; U.S. Pat. No. 6,083,725 to Selden et al.; U.S. Pat. No. 6,451,600 to Rasmussen et al.; U.S. Pat. No. 5,236,838 to Rasmussen et al.; and U.S. Pat. No. 5,879,680 to Ginns et al.), human placenta, or animal milk (see U.S. Pat. No. 6,188,045 to Reuser et al.). After the infusion, the exogenous enzyme is expected to be taken up by tissues through non-specific or receptor-specific mechanism. In general, the uptake efficiency (without use of an ASSC) is not high, and the circulation time of the exogenous protein is short (Ioannu et al., Am. J. Hum. Genet. 2001; 68: 14-25). In addition, the exogenous protein is unstable and subject to rapid intracellular degradation in vitro.

Other synthesis techniques for obtaining GAA suitable for pharmaceutical may be found, for example, in U.S. Pat. Nos. 7,560,424 and 7,396,811 to Lebowitz et al., U.S. Published Application Nos. 2009/0203575, 2009/0029467, 2008/0299640, 2008/0241118, 2006/0121018, and 2005/0244400 to Lebowitz et al., U.S. Pat. Nos. 7,423,135, 6,534,300, and 6,537,785; International Published Application No. 2005/077093 and U.S. Published Application Nos. 2007/0280925, and 2004/0029779. These references are hereby incorporated by reference in their entirety.

In one embodiment, the GAA is alglucosidase alfa, which consists of the human enzyme acid α-glucosidase (GAA), encoded by the most predominant of nine observed haplotypes of this gene and is produced by recombinant DNA technology in a Chinese hamster ovary cell line. Alglucosidase alpha is available as Myozyme® and Lumizyme®, from Genzyme Corporation (Cambridge, Mass.).

ASSC may be obtained using synthesis techniques known to one of ordinary skill in the art. For example, ASSC that may be used in the present application, such as 1-DNJ may be prepared as described in U.S. Pat. Nos. 6,274,597 and 6,583,158, and U.S. Published Application No. 2006/0264467, each of which is hereby incorporated by reference in its entirety.

In one embodiment of the present application, the ASSC is α-homonojirimycin and the GAA is hrGAA (e.g., Myozyme® or Lumizyme®). In an alternative embodiment the ASSC is castanospermine and the GAA is hrGAA (e.g., Myozyme® or Lumizyme®). The ASSC (e.g. α-homonojirimycin and castanospermine) may be obtained from synthetic libraries (see, e.g., Needels et al., Proc. Natl. Acad. Sci. USA 1993; 90:10700-4; Ohlmeyer et al., Proc. Natl. Acad. Sci. USA 1993; 90:10922-10926; Lam et al., PCT Publication No. WO 92/00252; Kocis et al., PCT Publication No. WO 94/28028) which provide a source of potential ASSC's according to the present invention. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from e.g. Pan Laboratories (Bothell, Wash.) or MycoSearch (NC), or are readily producible. Additionally, natural and synthetically produced libraries and compounds are readily modified through Res. 1986; 155:119-29.

In one embodiment, ASSC's useful for the present invention are inhibitors of lysosomal enzymes and include glucose and galactose imino-sugar derivatives as described in Asano et al., J. Med. Chem. 1994; 37:3701-06; Dale et al., Biochemistry 1985; 24:3530-39; Goldman et al., J. Nat. Prod. 1996; 59:1137-42; Legler et al, Carbohydrate Res. 1986; 155:119-29. Such derivatives include those that can be purchased from commercial sources such as Toronto Research Chemicals, Inc. (North York, On. Canada) and Sigma.

5.4 Treatment of Pompe Disease with ERT and an ASSC

In accordance with the invention, there are provided methods of using GAA (e.g. rhGAA) in combination with an ASSC for the GAA. One embodiment of the present invention provides for combination therapy of GAA (e.g. hrGAA ERT) and an ASSC. For example, the ASSC chaperone 1-deoxynojirimycin-HCl binds to mutant GAA and increases the ability of the GAA to stabilize to a proper conformation.

One embodiment of the present invention provides a method for treating Pompe subset patients with the IVS 1 (−13 T>G) splicing defect with an ASSC and hrGAA enzyme replacement therapy. In cell lines derived from late-onset Pompe patients with this common splicing mutation, 1-deoxynojirimycin-HCl increased GAA levels alone and in combination with hrGAA.

In one non-limiting embodiment of the present invention, 1-deoxynojirimycin-HCl, or a pharmaceutically acceptable salt thereof, can be administered to a subject in a dose of between about 10 mg/kg to 1000 mg/kg, preferably administered orally, either prior to, concurrent with, or after administration of the GAA. In one non-limiting embodiment, 1-deoxynojirimycin-HCl and recombinant human GAA show surprising efficacy on cellular enzyme activity, glycogen reduction and the treatment of Pompe disease. In rats, the plasma half-life of recombinant human GAA (rhGAA) increased 2-fold when 1-deoxynojirimycin-HCl (30 mg/kg p.o.) was administered in a dosing regimen that includes dosing 30 minutes prior to rhGAA injection. In GAA KO mice, the uptake of rhGAA was increased approximately 2-fold in heart and diaphragm when 1-deoxynojirimycin-HCl (100 mg/kg p.o.) was in a dosing regimen that includes administration prior to rhGAA injection. These results indicate that co-administration of a an ASSC with rhGAA increase the enzyme's exposure and tissue uptake in vivo in surprising amounts.

For example, one embodiment of the present invention provides a method of treating Pompe Disease comprising administering GAA (e.g. rhGAA) bi-weekly, weekly or once per two weeks for up to about 10 weeks in combination with from about 1 to about 5000 mg/kg of an ASSC (e.g., 1-DNJ-HCl) prior to, and in regular intervals after, the GAA infusion. For example, the ASSC could be administered within two hours of the infusion, and then administered at regular intervals once, twice, three-times, four-times, five-times or six-times within 24 hours post-infusion.

In one particular embodiment, the GAA is Myozyme® and is administered via infusion once per week and the ASSC (e.g., 1-DNJ-HCl) is administered at 10 mg/kg, 100 mg/kg or 1000 mg/kg 30 minutes prior to infusion, and then 8, 16, and 24 hours after each Myozyme® infusion.

In other particular embodiments, the GAA is Lumizyme® and is administered via infusion once per week and the ASSC (e.g., 1-DNJ-HCl) is administered at 10 mg/kg, 100 mg/kg or 1000 mg/kg 30 minutes prior to infusion, and then 8, 16, and 24 hours after each Lumizyme® infusion.

While not being bound by any particular theory, it is believed that acid α-glucosidase (GAA) functions to remove terminal glucose residues from lysosomal glycogen. Some genetic mutations reduce GAA trafficking and maturation. The pharmacological chaperone 1-DNJ increases GAA levels by selectively binding and stabilizing the enzyme in a proper conformation which restores proper protein trafficking to the lysosome.

In alternative embodiments, the ASSC is administered as described in International Publication No. 2008/134628, which is hereby incorporated by reference in its entirety.

In some embodiments, the route of administration is subcutaneous. Other routes of administration may be oral or parenteral, including intravenous, intra-arterial, intraperitoneal, ophthalmic, intramuscular, buccal, rectal, vaginal, intraorbital, intracerebral, intradermal, intracranial, intraspinal, intraventricular, intrathecal, intracisternal, intracapsular, intrapulmonary, intranasal, transmucosal, transdermal, or via inhalation. Intrapulmonary delivery methods, apparatus and drug preparation are described, for example, in U.S. Pat. Nos. 5,785,049, 5,780,019, and 5,775,320, each incorporated herein by reference. In some embodiments, the method of intradermal delivery is by iontophoretic delivery via patches; one example of such delivery is taught in U.S. Pat. No. 5,843,015, which is incorporated herein by reference.

Administration may be by periodic injections of a bolus of the preparation, or as a sustained release dosage form over long periods of time, or by intravenous or intraperitoneal administration, for example, from a reservoir which is external (e.g., an IV bag) or internal (e.g., a bioerodable implant, a bioartificial organ, or a population of implanted GAA production cells). See, e.g., U.S. Pat. Nos. 4,407,957 and 5,798,113, each incorporated herein by reference. Intrapulmonary delivery methods and apparatus are described, for example, in U.S. Pat. Nos. 5,654,007, 5,780,014, and 5,814,607, each incorporated herein by reference. Other useful parenteral delivery systems include ethylene-vinyl acetate copolymer particles, osmotic pumps, implantable infusion systems, pump delivery, encapsulated cell delivery, liposomal delivery, needle-delivered injection, needle-less injection, nebulizer, aeorosolizer, electroporation, and transdermal patch. Needle-less injector devices are described in U.S. Pat. Nos. 5,879,327; 5,520,639; 5,846,233 and 5,704,911, the specifications of which are herein incorporated by reference. Any of the GAA preparation described herein can administered in these methods.

Delivery of the formulation can be continuous over a pre-selected administration period ranging from several hours, one to several weeks, one to several months, or up to one or more years. In certain embodiments, the dosage form is one that is adapted for delivery of GAA over an extended period of time. Such delivery devices may be adapted for administration of GAA for several hours (e.g., 2 hours, 12 hours, or 24 hours to 48 hours or more), to several days (e.g., 2 to 5 days or more, from about 100 days or more), to several months or years. In some of these embodiments, the device is adapted for delivery for a period ranging from about 1 month to about 12 months or more. The GAA delivery device may be one that is adapted to administer GAA to an individual for a period of, e.g., from about 2 hours to about 72 hours, from about 4 hours to about 36 hours, from about 12 hours to about 24 hours; from about 2 days to about 30 days, from about 5 days to about 20 days, from about 7 days to about 100 days or more, from about 10 days to about 50 days; from about 1 week to about 4 weeks; from about 1 month to about 24 months or more, from about 2 months to about 12 months, from about 3 months to about 9 months; or other ranges of time, including incremental ranges, within these ranges, as needed.

In certain embodiments, the methods of the invention include administering to an individual, for example, subcutaneous administration, a dose of from about 0.1 to about 50 mg/kg of GAA, wherein the dose is administered once per day, once every two days, once every three days, once every four days, once every five days, or once every six days. In certain embodiments, the formulation of the present application is administered once per week, twice per week, three times per week, four times per week, five times per week, six times per week or seven times per week.

In certain embodiments, the methods of the present application comprise administering a co-formulation to an individual comprising GAA and an ASSC, wherein the co-formulations is administered subcutaneously. In certain embodiments, the dose of GAA in the co-formulation is between about 0.1 and about 5000 mg/kg, or between about 10 and about 4000 mg/kg, or between about 25 and about 3000 mg/kg, or between about 50 and about 2000 mg/kg, or between about 100 and about 1000 mg/kg, or between about 200 and about 500 mg/kg.

In certain embodiments, the dose of GAA in the co-formulation is between about 0.1 and about 100 mg/kg, or between about 1 and about 80 mg/kg, or between about 5 and about 50 mg/kg, or between about 10 and about 40 mg/kg, or between about 15 and about 25 mg/kg.

In certain embodiments, the dose of rhGAA in the co-formulation is about 20 mg/kg.

In certain embodiments, the dose of ASSC in the co-formulation is between about 0.1 and about 5000 mg/kg, or between about 10 and about 4000 mg/kg, or between about 25 and about 3000 mg/kg, or between about 50 and about 2000 mg/kg, or between about 100 and about 1000 mg/kg, or between about 200 and about 500 mg/kg.

In certain embodiments, the dose of ASSC in the co-formulation is between about 0.1 and about 100 mg/kg, or between about 1 and about 80 mg/kg, or between about 5 and about 50 mg/kg, or between about 10 and about 40 mg/kg, or between about 15 and about 25 mg/kg.

In certain embodiments, the dose of ASSC in the co-formulation is about 30 mg/kg.

In certain embodiments, the dose does not result in a toxic level of GAA in the liver of the individual. In some embodiments, the GAA is administered in a sufficient dose to result in a peak concentration of GAA in tissues of the subject, for example muscle tissue, within about 24 hours after the administration of the dose. In certain embodiments, the GAA is administered in a sufficient dose to result in a peak concentration of GAA in tissues of the subject within about 10 to about 50 hours, or about 45, 40, 35, 30, 25, or fewer hours after the administration of the dose. In some embodiments, the formulation of the GAA is a single-dose formulation. In some embodiments, the formulation of the GAA is a multi-dose formulation.

A GAA preparation of the present invention can be formulated such that the total required dose may be administered in a single subcutaneous injection of one or more milliliters, for example, 1, 2, 3, 4, 5, 6, 7, 8, 9, 10 or more milliliters. The preparation can be formulated to be administered subcutaneously at several different injection sites. In order to allow an injection volume of one or two milliliters, a GAA preparation of the present invention may be formulated at a concentration in which the preferred dose is delivered in a volume of one to two milliliters. Subcutaneous injections of GAA preparations have the advantages of being convenient for the patient, in particular by allowing self-administration, while also resulting in a prolonged plasma half-life as compared to, for example, intravenous administration. A prolongation in plasma half-life results in maintenance of effective plasma GAA levels over longer time periods, the benefit of which is to increase the exposure of clinically affected tissues to the injected GAA and, as a result, may increase the uptake of GAA into such tissues. This allows a more beneficial effect to the patient and/or a reduction in the frequency of administration. Furthermore, a variety of devices designed for patient convenience, such as refillable injection pens and needle-less injection devices, may be used with the GAA preparations of the present invention as discussed herein. Because the GAA co-formulated with an ASSC is stable at room temperature for extended periods of time, the preparation can be held in a cartridge aside the patient's body to allow for recurring low dose administration or continuous low volume administration to provide for a steady state of enzyme administration. Such administration may avoid the potential side effects of high doses of enzyme replacement therapy (ERT) administered during an intravenous infusion.

5.5 Pharmaceutical Compositions

The compounds and compositions of the invention may be formulated as pharmaceutical compositions by admixture with a pharmaceutically acceptable carrier or excipient.

In one embodiment, an ASSC and GAA are formulated in a single composition (i.e., a co-formulation). Such a composition enhances stability of GAA both during storage (i.e., in vitro) and in vivo after administration to a subject, thereby increasing circulating half-life, tissue uptake, and resulting in increased therapeutic efficacy of GAA. The formulation is preferably suitable for parenteral administration, including intravenous, subcutaneous, and intraperitoneal administration, however, formulations suitable for other routes of administration such as oral, intranasal, or transdermal are also contemplated.

The present invention features liquid pharmaceutical formulations (e.g., formulations comprising GAA and an ASSC) having improved properties as compared to art-recognized formulations. The present invention is based on the surprising finding that by combining an ASSC with GAA, the concentration of GAA in a formulation can be increased to an amount that would normally result in the formation of GAA aggregates in the absence of an ASSC. Despite the high concentration of GAA, the formulation of the invention is able to maintain solubility and stability of the GAA, e.g., during manufacturing, storage, and/or repeated freeze/thaw processing steps or extended exposure to increased air-liquid interfaces. In addition, the formulation of the invention maintains a low level of protein aggregation (e.g., less than about 5%, 4%, 3%, 2%, or less than about 1%), despite having a high concentration of GAA. The formulation of the invention also surprisingly maintains a low viscosity within ranges suitable for subcutaneous injection, despite having a high concentration of GAA.

The present invention also provides for very potent and concentrated GAA formulations that can be achieved by solubilizing the GAA in a small volume by combining the GAA with an ASSC. The formulations of the invention are of particular use where the delivery device is relatively small (e.g., an implantable system), where delivery is required for a relatively long duration, or where high effective doses of GAA are required to achieve the desired therapeutic effect. Thus, it is possible to deliver a consistent amount of GAA over an extended period of time (e.g., days, weeks, months, etc.) without the need to refill or replace the delivery device, thereby reducing risk of infection and tissue damage, increasing patient compliance, and achieving consistent, accurate dosing.

In certain embodiments of the present invention, therapeutic amounts of GAA (even high doses) can be delivered to a subject by using only very small volumes of GAA (e.g., on the order of microliters per day or nanoliters per day). In certain body tissues, e.g., subcutaneous space, low volume delivery facilitates better absorption of the GAA by the local tissue, and minimizes local tissue disturbance, trauma, or edema.

In certain embodiments, formulations of the invention include high concentrations of GAA such that the liquid formulation does not show significant opalescence, aggregation, or precipitation.

In another embodiment, formulations of the invention include high concentrations of GAA such that are suitable for, e.g., subcutaneous administration without significant felt pain (e.g., as determined by a visual analog scale (VAS) score).

In certain embodiments, the formulations of the invention comprise a high GAA concentration, including, for example, a GAA concentration of about 25 mg/mL, or about 50 mg/mL, or about 80 mg/mL, or about 100 mg/mL, or about 115 mg/mL, or about 150 mg/ml, or about 160 mg/ml or about 200 mg/mL, or about 240 mg/mL, or about 250 mg/mL. For example, as described in Example 10 below, in one aspect of the invention the liquid pharmaceutical formulation comprises a human recombinant wild-type GAA concentration of about 25 mg/mL. It is also contemplated that the formulations of the invention may comprise a GAA concentration between about 1 mg/mL and about 500 mg/mL, or between about 5 mg/mL and about 500 mg/mL, or between about 5 mg/mL and about 250 mg/mL, or between about 10 mg/mL and about 200 mg/mL, or between about 20 mg/mL and about 100 mg/mL, or between about 1 mg/mL and about 60 mg/mL. Concentrations and ranges intermediate to the above recited concentrations are also intended to be part of this invention (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 mg/mL).

In certain embodiments, a formulation of the invention comprises a GAA in a concentration that is greater then 5 mg/mL.

In certain embodiments, a formulation of the invention comprises an ASSC in an amount effective to reduce or inhibit aggregation of GAA in the formulation. Such an amount of ASSC includes, for example, between about 0.005 mM and 100 mM, or between about 0.05 mM and about 90 mM, or between about 0.1 mM and about 80 mM, or between about 0.5 mM and about 70 mM, or between about 1 mM and about 60 mM, or between about 2 mM and about 50 mM, or between about 3 mM and about 40 mM, or between about 4 mM and about 30 mM, or between about 5 mM and about 20 mM. In certain embodiments, the ASSC is present in the formulations of the invention at a concentration of between about 0.5 and about 20 mM. In certain embodiments, the ASSC is present in the formulations of the invention at a concentration of about 1 mM. In certain embodiments, the ASSC is present in the formulations of the invention at a concentration of about 10 mM.

In certain embodiments, a formulation of the invention comprises an ASSC in an amount effective to reduce or inhibit aggregation of GAA in the formulation. Such an amount of ASSC includes, for example, between about 5 and about 500 mg/mL, or between about 10 and about 250 mg/mL, or between about 20 and about 200 mg/mL, or between about 30 and about 150 mg/mL, or between about 40 and about 100 mg/mL, or between about 50 and about 75 mg/mL. In certain embodiments, the ASSC is present in an amount of between about 5 and about 200 mg/mL.

In certain embodiments, the ASSC is present in the formulation at a concentration of about 32 mg/mL or about 160 mg/mL.

In certain embodiments of the invention, a liquid formulation comprising DNJ and GAA is prepared by dissolving DNJ in water to achieve a concentration of 10 mM DNJ. GAA can be reconstituted in 1.8 ml water, and dialyzed overnight in phosphate buffered-saline (pH 7.4). 4.4 microliters of DNJ (10 mM) can then be added to 400 microliters of GAA, such that the GAA is at a concentration of 25 mg/ml.

In another embodiment, the GAA and the ASSC are formulated in separate compositions. In this embodiment, the chaperone and the replacement protein may be administered according to the same route, e.g., intravenous infusion, or different routes, e.g., intravenous infusion for the replacement protein, and oral administration for the ASSC.

The pharmaceutical formulations suitable for injectable use include sterile aqueous solutions (where water soluble) or dispersions and sterile powders for the extemporaneous preparation of sterile injectable solutions or dispersion. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The preventions of the action of microorganisms can be brought about by various antibacterial and antifungal agents, for example, parabens, chlorobutanol, phenol, benzyl alcohol, sorbic acid, and the like.

In many cases, it will be preferable to include isotonic agents, for example, sugars or sodium chloride. Prolonged absorption of the injectable compositions can be brought about by the use in the compositions of agents delaying absorption, for example, aluminum monosterate and gelatin. Sterile injectable solutions may be prepared by incorporating the GAA and ASSC in the required amounts in the appropriate solvent with various of the other ingredients enumerated above, as required, followed by filter or terminal sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

Preferably the formulation may contain one or more excipients. Pharmaceutically acceptable excipients which may be included in the formulation are buffers such as citrate buffer, phosphate buffer (such as, for example, monobasic sodium phosphate, dibasic sodium phosphate and combinations thereof), acetate buffer, bicarbonate buffer, amino acids, urea, alcohols, ascorbic acid, phospholipids; proteins, such as serum albumin, collagen, and gelatin; salts such as EDTA or EGTA, and sodium chloride; liposomes; polyvinylpyrollidone; sugars, such as dextran, mannitol, sorbitol, and glycerol; propylene glycol and polyethylene glycol (e.g., PEG-4000, PEG-6000); glycerol; glycine or other amino acids; and lipids. Buffer systems for use with the formulations include citrate; acetate; bicarbonate; and phosphate buffers.

In certain embodiments, the formulations of the present application further comprise an excipient selected from the group consisting of polyethylene glycol (PEG), PEG-400, arginine, arginine and glutamic acid, proline, gamma-cyclodextrin and combinations thereof.

In certain embodiments, the buffer and/or excipient is present in the formulation at a concentration of between about 1 and about 50% weight/volume (w/v), or between about 2 and about 40% w/v, or between about 3 and about 30% w/v, or between about 4 and about 20% w/v, or between about 5 and about 10% w/v.

In certain embodiments, the buffer and/or excipient is present in the formulation at a concentration of between about 1 and about 500 mM, or between about 10 and about 400 mM, or between about 20 and about 300 mM, or between about 30 and about 250 mM, or between about 40 and about 200 mM, or between about 50 and about 150 mm, or between about 60 and about 100 mM.

In certain embodiments, the formulation comprises phosphate buffer present at a concentration of about 26 mM.

In certain embodiments, the formulation comprises citrate buffer present at a concentration of about 150 mM.

In certain embodiments, the formulation comprises PEG-400 present at a concentration of about 5% w/v.

In certain embodiments, the formulation comprises arginine present at a concentration of about 100 mM.

In certain embodiments, the formulation comprises arginine at a concentration of about 50 mM and glutamic acid present at a concentration of about 50 mM.

In certain embodiments, the formulation comprises proline present at a concentration of about 250 mM.

In certain embodiments, the formulation comprises gamma-cyclodextrin present at a concentration of about 10% w/v.

The formulation also may contain a non-ionic detergent. Preferred non-ionic detergents include Polysorbate 20, Polysorbate 80, Triton X-100, Triton X-114, Nonidet P-40, Octyl α-glucoside, Octyl β-glucoside, Brij 35, Pluronic, and Tween 20.

For lyophilization of protein and chaperone preparations, the protein concentration can be 0.1-10 mg/mL. Bulking agents, such as glycine, mannitol, albumin, and dextran, can be added to the lyophilization mixture. In addition, possible cryoprotectants, such as disaccharides, amino acids, and PEG, can be added to the lyophilization mixture. Any of the buffers, excipients, and detergents listed above, can also be added.

The route of administration may be oral or parenteral, including intravenous, subcutaneous, intra-arterial, intraperitoneal, ophthalmic, intramuscular, buccal, rectal, vaginal, intraorbital, intracerebral, intradermal, intracranial, intraspinal, intraventricular, intrathecal, intracisternal, intracapsular, intrapulmonary, intranasal, transmucosal, transdermal, or via inhalation.

Administration of the above-described parenteral formulations may be by periodic injections of a bolus of the preparation, or may be administered by intravenous or intraperitoneal administration from a reservoir which is external (e.g., an i.v. bag) or internal (e.g., a bioerodable implant, a bioartificial organ, or a population of implanted cells that produce the replacement protein). See, e.g., U.S. Pat. Nos. 4,407,957 and 5,798,113, each incorporated herein by reference. Intrapulmonary delivery methods and apparatus are described, for example, in U.S. Pat. Nos. 5,654,007, 5,780,014, and 5,814,607, each incorporated herein by reference. Other useful parenteral delivery systems include ethylene-vinyl acetate copolymer particles, osmotic pumps, implantable infusion systems, pump delivery, encapsulated cell delivery, liposomal delivery, needle-delivered injection, needle-less injection, nebulizer, aeorosolizer, electroporation, and transdermal patch. Needle-less injector devices are described in U.S. Pat. Nos. 5,879,327; 5,520,639; 5,846,233 and 5,704,911, the specifications of which are herein incorporated by reference. Any of the formulations described above can administered in these methods.

5.6 In Vitro Stability

Ensuring the stability of GAA formulations during its shelf life is a major challenge. For example, the patient instructions for Myozyme® and Lumizyme® notes that vials are for single use only and that unused product should be discarded. The instructions further state that Myozyme® and Lumizyme® should be reconstituted, diluted, and administered by a health care professional, and that administration should be without delay. Myozyme® and Lumizyme® must be stored at 2 to 8° C., and the product is only stable for up to 24 hours at these temperatures.

When an ASSC and the GAA are present in the same composition, the formulated compositions of the invention provide more stable compositions. In addition to stabilizing the administered protein in vivo, the ASSC reversibly binds to and stabilizes the conformation of the GAA in vitro, thereby preventing aggregation and degradation, and extending the shelf-life of the formulation. Analysis of the ASSC/replacement protein interaction may be evaluated using techniques well-known in the art, such as, for example, differential scanning calorimetry, or circular dichroism.

For example, where an aqueous injectable formulation of the composition is supplied in a stoppered vial suitable for withdrawal of the contents using a needle and syringe, the presence of an ASSC inhibits aggregation of the GAA. The vial could be for either single use or multiple uses. The formulation can also be supplied as a prefilled syringe, an autoinjector pen, or a needle-free administration device. In another embodiment, the formulation is in a dry or lyophilized state, which would require reconstitution with a standard or a supplied, physiological diluent to a liquid state. In this instance, the presence of an ASSC stabilizes the GAA during and post-reconstitution to prevent aggregation. In the embodiment where the formulation is a liquid for intravenous administration, such as in a sterile bag for connection to an intravenous administration line or catheter, the presence of an ASSC confers the same benefit.

In addition to stabilizing the replacement protein to be administered, the presence of an ASSC enables the GAA formulation to be stored at a neutral pH of about 7.0-7.5. This confers a benefit to proteins that normally must be stored at a lower pH to preserve stability. For example, lysosomal enzymes, such as GAA, typically retain a stable conformation at a low pH (e.g., 5.0 or lower). However, extended storage of the replacement enzyme at a low pH may expedite degradation of the enzyme and/or formulation.

As described above, the liquid formulation of the invention has advantageous stability and storage properties. Stability of the liquid formulation is not dependent on the form of storage, and includes, but is not limited to, formulations which are frozen, lyophilized, spray-dried, or formulations which in which the active ingredient is suspended. Stability can be measured at a selected temperature for a selected time period. In one aspect of the invention, the protein in the liquid formulations is stable in a liquid form for at least about 1 week; at least about 2 weeks; at least about 3 weeks; at least about 1 month; at least about 2 months; at least about 3 months; at least about 4 months, at least about 5 months; at least about 6 months; at least about 12 months; at least about 18 months. Values and ranges intermediate to the above recited time periods are also intended to be part of this invention, e.g., about 3, 4, 5, 6, 7, 8, 9, 10, 11, 12, 13, 14, 15, 16, 17, 18, 19, 20, 21, 22, 23, or about 24 months. In addition, ranges of values using a combination of any of the above recited values as upper and/or lower limits are intended to be included. In certain embodiments, the formulation is stable at room temperature (about 30° C.) or at about 37° C., or at about 40° C., or at about 45° C. for at least about 1 month and/or stable at about 2-8° C. for at least about 1 year, or more preferably stable at about 2-8° C. for at least about 2 years. Furthermore, the formulation is preferably stable following freezing (to, e.g., −80° C.) and thawing of the formulation, hereinafter referred to as a "freeze/thaw cycle."

Stability of a protein (e.g., protein stability and/or reduction in contamination) in a liquid formulation may also be defined as the percentage of monomer, aggregate, or fragment, or combinations thereof, of the protein in the formulation. A protein "retains its physical stability" in a formulation if it shows substantially no signs of aggregation, precipitation and/or denaturation upon visual examination of color and/or clarity, or as measured by UV light scattering or by size exclusion chromatography, non-denaturing PAGE, or other methods for determining size, etc. In one aspect of the invention, a stable liquid formulation is a formulation having less than about 10%, or less than about 5%, or less than about 1% of the protein being present as aggregate in the formulation.

In one embodiment, the physical stability of a liquid formulation is determined by determining turbidity of the formulation following a stir stress assay, e.g., 24 hour or 48-hour stir-stress assay. For example, a stir stress assay may be performed by placing a suitable volume of a liquid formulation in a beaker with a magnetic stirrer, e.g., (multipoint HP, 550 rpm), removing aliquots at any suitable time, e.g., at T0-T48 (hrs), and performing suitable assays as desired on the aliquots. Samples of a formulation under the same conditions but without stirring serve as control.

Turbidity measurements may be performed using a laboratory turbidity measurement system from Hach (Germany) and are reported as nephelometric units (NTU).

Stability of the composition (e.g., protein stability and/or reduction in contamination) can also be measured, e.g., by measuring protein degradation or contaminant growth or presence. Protein degradation can be determined, e.g., by reverse phase HPLC, non-denaturing PAGE, ion-exchange chromatography, peptide mapping, or similar methods.

The stability of GAA in the presence of an ASSC, at a concentration described herein, can be measured, e.g., as a percent aggregation or degradation, at a predetermined time and compared with one or more standards. For example, a suitable standard is a composition similar to the test conditions except that the GAA is not contacted with an ASSC. The stabilities of the GAA at a concentration are compared. Suitability can be shown by the GAA at a particular concentration in combination with an ASSC having comparable or better stability than in the absence of the ASSC.

5.7 In Vivo Stability

As described above for the in vitro formulations, the presence of an ASSC for the GAA has the benefit of prolonging in plasma the half-life of the exogenous GAA, thereby maintaining effective replacement protein levels over longer time periods, resulting in increased exposure of clinically affected tissues to the GAA and, thus, increased uptake of protein into the tissues. This confers such beneficial effects to the patient as enhanced relief, reduction in the frequency, and/or reduction in the amount administered. This will also reduce the cost of treatment.

In addition to stabilizing wild-type replacement GAA, the ASSC will also stabilize and enhance expression of endogenous mutant GAA that are deficient as a result of mutations that prevent proper folding and processing in the ER, as in conformational disorders such as Pompe Disease.

The present invention is not to be limited in scope by the specific embodiments described herein and the Examples that follow. Indeed, various modifications of the invention in addition to those described herein will become apparent to those skilled in the art from the foregoing description and the accompanying Examples and Figures. Such modifications are intended to fall within the scope of the appended claims.

EXAMPLES

Example 1: In Vitro Thermal Stability of rhGAA and 100 µM 1-DNJ-HCl

The stability of recombinant human GAA (Myozyme®, Genzyme Corp.) with and without 100 µM of the ASSC 1-deoxynojirimycin hydrochloride (1-DNJ-HCl) was determined via a thermal stability assay that utilizes heat to induce protein denaturation. Denaturation is monitored using a SYPRO Orange dye that fluoresces upon binding to hydrophobic amino acids (which are not exposed in a folded protein).

Figure 1:
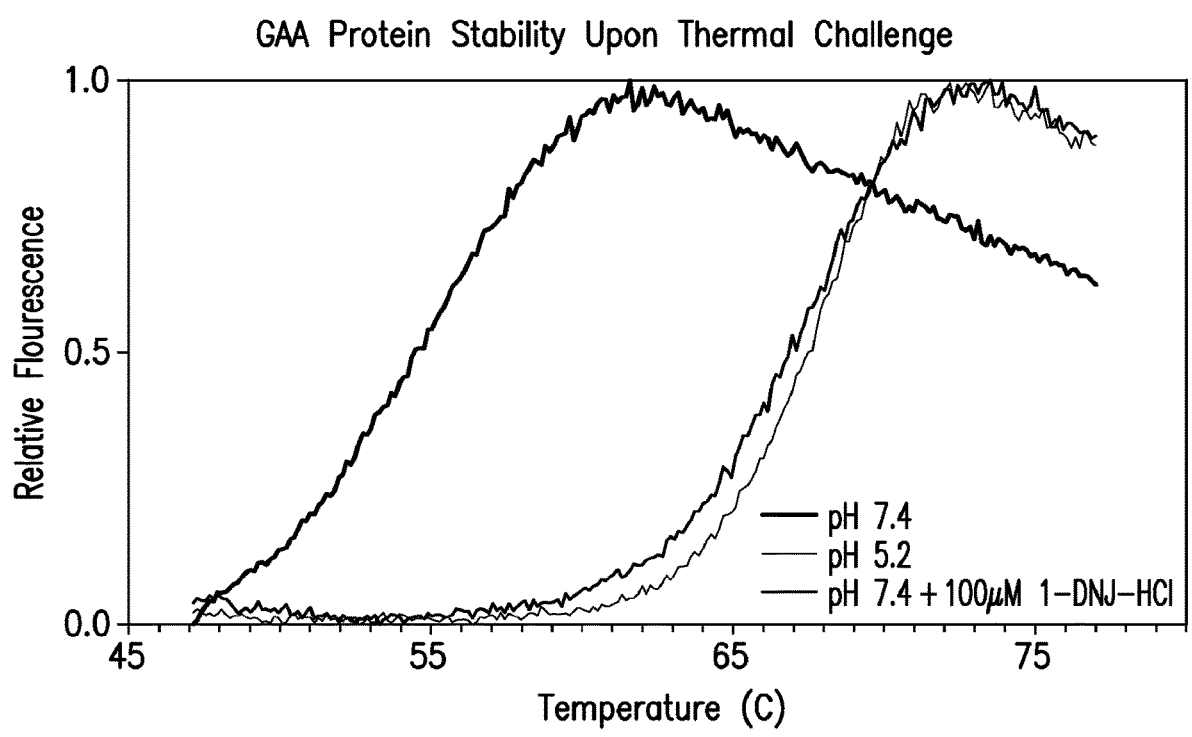

The thermal stability was performed at pH 7.4 for two formulations, which corresponds to the pH of the ER. As shown in FIG. 1, the formulation that contains 100 µM of 1-DNJ-HCl at 7.4 pH required significantly more heat to denature, and is thus more stable, as compared to formulation without the ASSC at 7.4 pH.

Example 2: GAA Residual Activity and Thermal Stability of rhGAA and 50 µM 1-DNJ-HCl Residual GAA activity was determined for four formulations:
(1) Myozyme® alone at pH 7.4;
(2) Myozyme® plus 50 µM 1-DNJ-HCl at pH 7.4;
(3) Myozyme® alone at pH 5.2;
(4) Myozyme® plus 50 µM 1-DNJ-HCl at pH 5.2.

Activity was measured, based on the % of initial activity (t=0) over 24 hours. Samples were assayed for GAA enzyme activity based on the hydrolysis of the fluorogenic substrate 4-MU-α-glucose at 0, 3, 6 and 24 hours. The GAA activity was expressed as % of initial activity, i.e. residual activity.

Figure 2A:
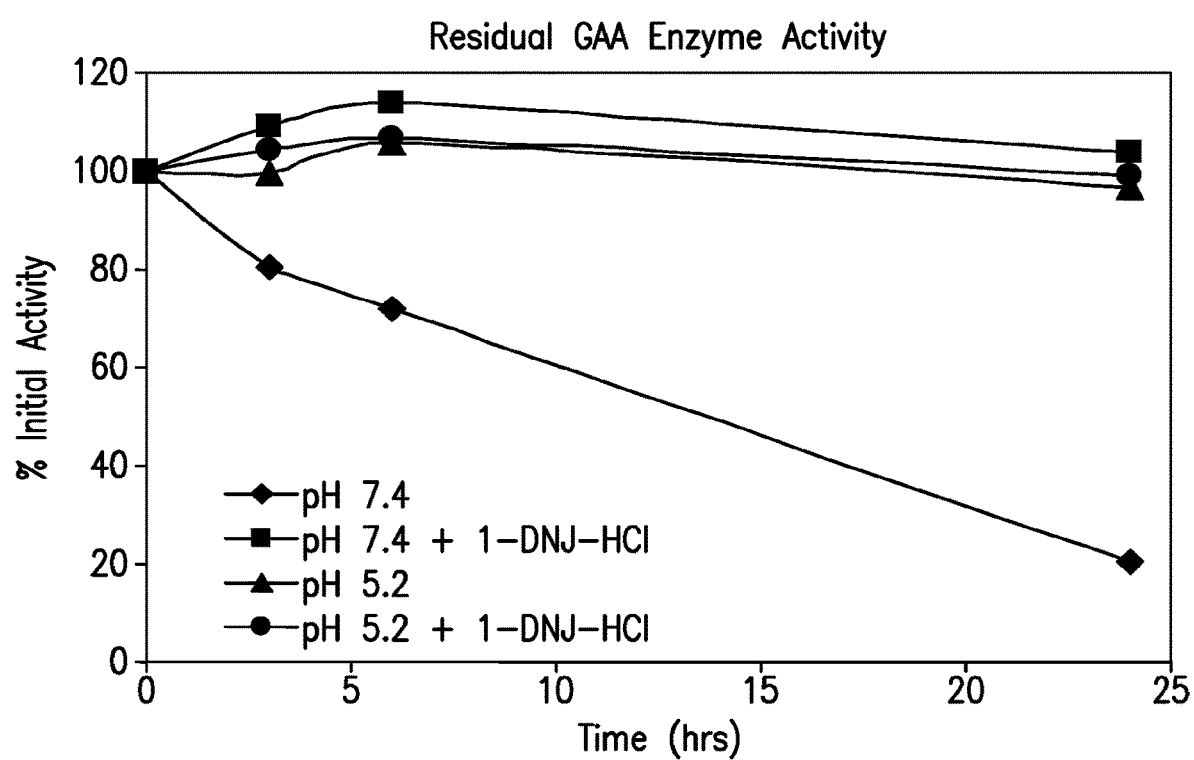

As shown in FIG. 2A, formulation (1) above (without the ASSC) lost activity over time, having only about 20% of its initial activity 24 hours after administration. In contrast, formulation (2) maintained most, if not all of its initial activity over 24 hours. Both formulations at ph 5.2 (formulations (3) and (4) above) maintained most of their initial activity over 24 hours.

Figure 2B:
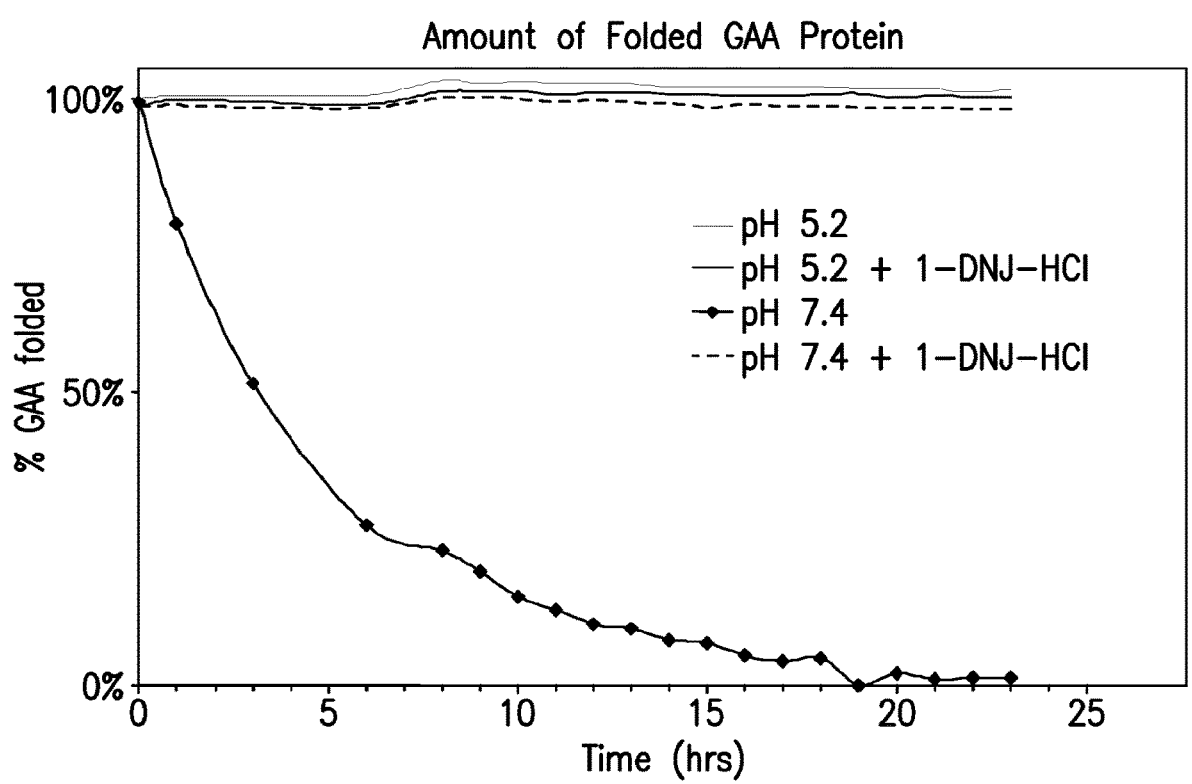

In order to determine if loss of initial enzyme activity is correlated to failure to maintain a proper conformation, a SYPRO Orange thermal stability experiment was performed on the samples above as generally described in Example 1. In this thermal stability experiment, however, the concentration of 1-DNJ-HCl was increased to 100 µM in formulations (2) and (4). Based on this experiment, the % of GAA folded was estimated and plotted in FIG. 2B. The decrease in the amount of folded GAA over 24 hours in FIG. 2B for the formulation (1) correlates to the loss of activity shown in FIG. 2A for this same general formulation.

Figure 3:
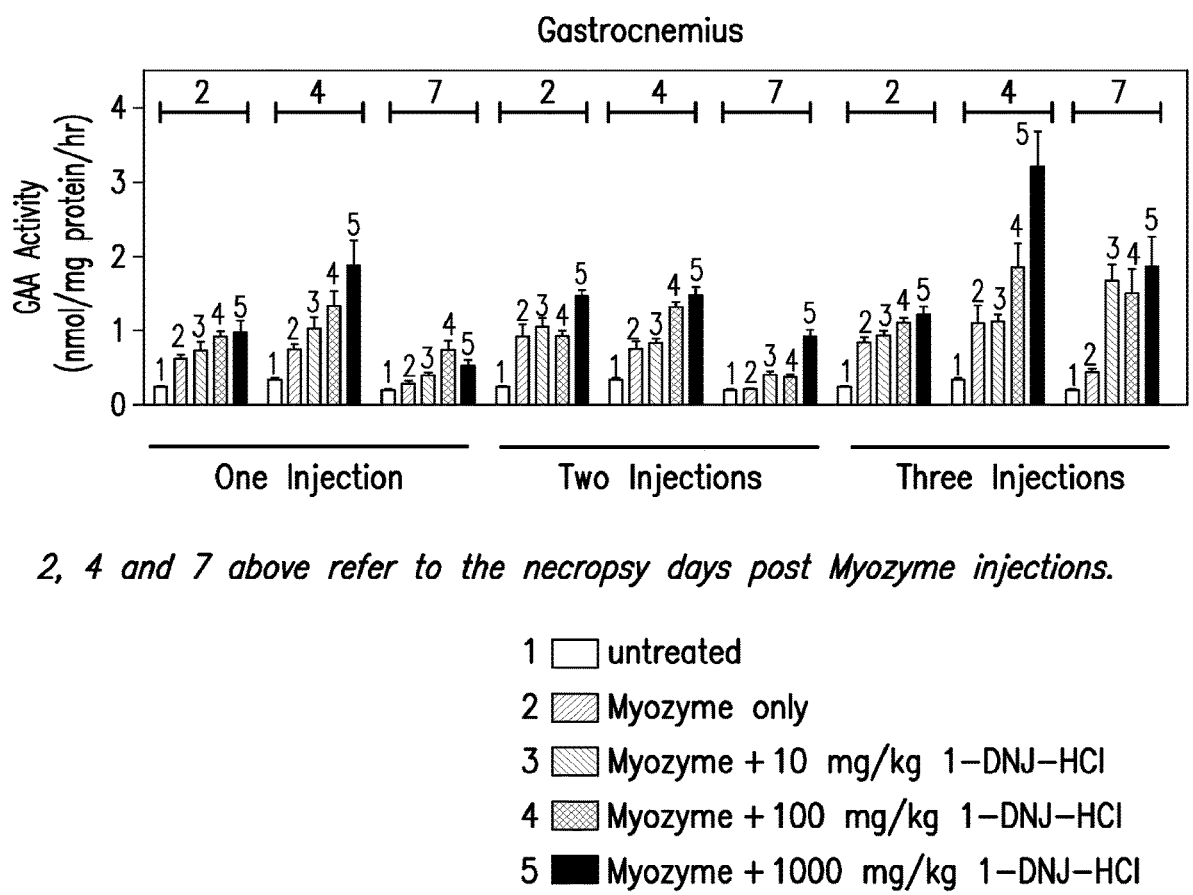
Figure 4:
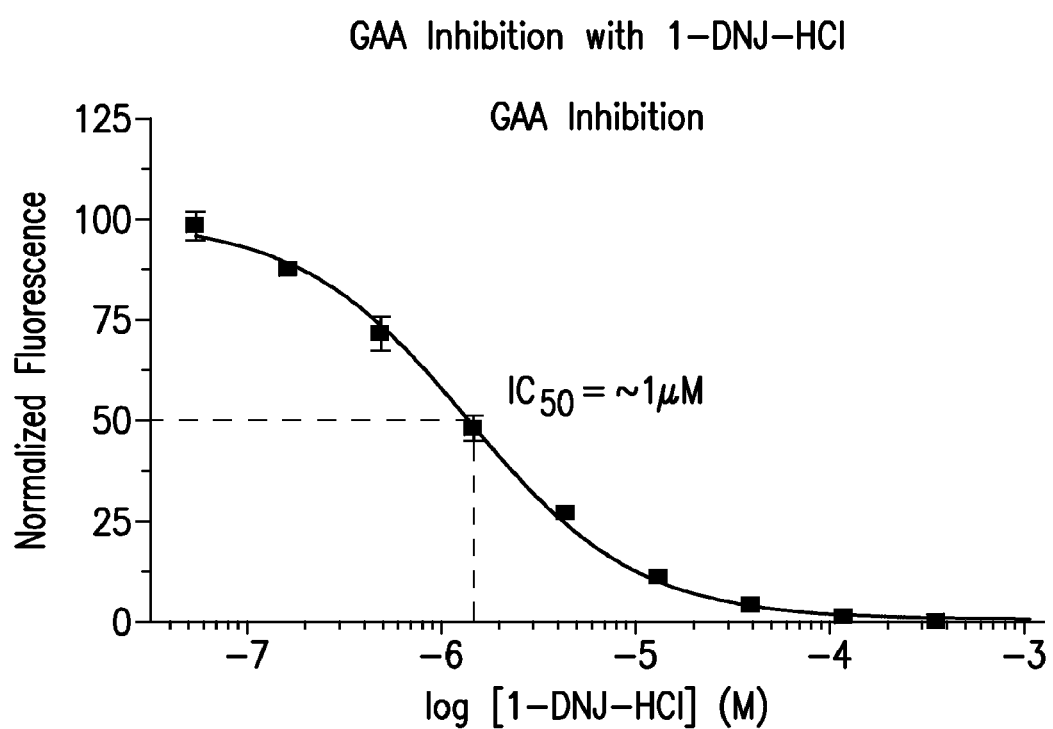

Example 3: In Vivo Uptake of Myozyme® in GAA KO Mice with and without Oral Administration of 1-DNJ-HCl Five groups of GAA KO mice were administered one of the following formulations:
(1) untreated control;
(2) 10 mg/kg of Myozyme® IV once per week, for up to three weeks
(3) Myozyme® infusion as in (2), plus 10 mg/kg of 1-DNJ-HCl;
(4) Myozyme® infusion as in (2), plus 100 mg/kg of 1-DNJ-HCl;
(5) Myozyme® infusion as in (2), plus 1000 mg/kg of 1-DNJ-HCl;

Tissue homogenates were generated for analysis. Enzymatic activity as determined using a 4-MUG fluorogenic substrate assay. The results are shown in FIG. 3.

These results indicate that Myozyme® tissue uptake (as a measure of GAA activity) declined at 7 days post injection for all groups. Coadministration of 1-DNJ-HCl with Myozyme® facilitated a dose-dependent increase in Myozyme® uptake for up to 7 days post injection. The effect of 1-DNJ-HCl was more pronounced and significant ($p<0.05$ t-test vs. Myozyme® alone) at 4 and 7 days post injection of either 1, 2, or 3 doses.

Figure 5:
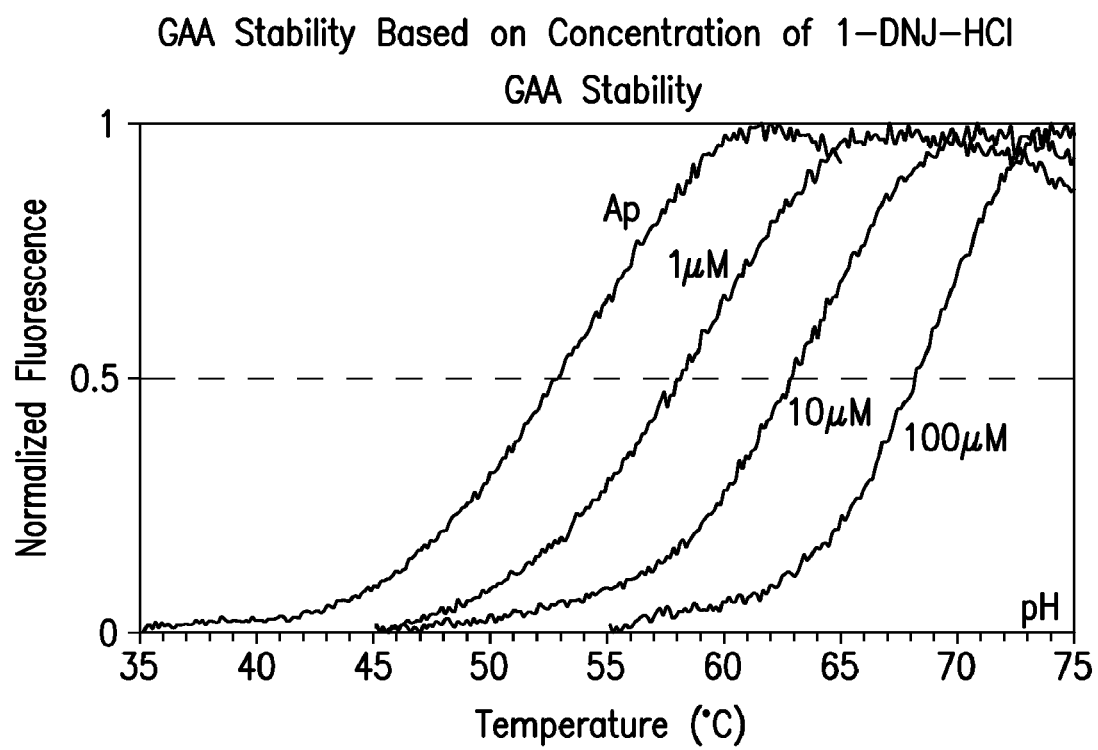

Example 4: In Vivo Uptake of Myozyme® in GAA KO Mice with and without Oral Administration of 1-DNJ-HCl A thermal stability experiment as generally described in Example 1 was performed on four compositions:
(1) Myozyme® only composition;
(2) Myozyme® plus 1 µM of 1-DNJ-HCl;
(3) Myozyme® plus 10 µM of 1-DNJ-HCl;
(4) Myozyme® plus 100 µM of 1-DNJ-HCl;

As shown in FIG. 5, DNJ-HCl increases GAA thermostability as evident by increases in GAA's melting temperature in a dose-dependent manner.

Figure 6:
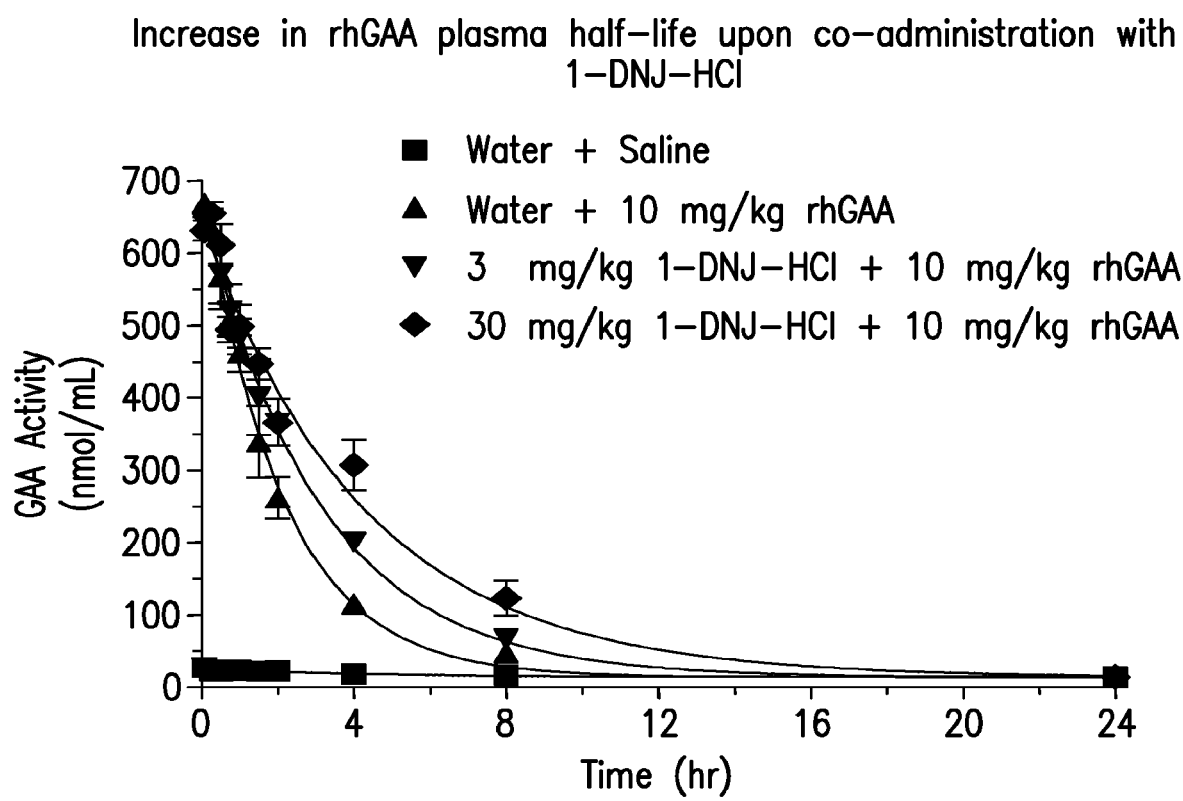

Example 5: In Vivo Half-Life of rhGAA in Rats when Administered as Monotherapy, or when Combined with 1-DNJ-HCl Four groups of rats were administered one of the following dosing regimens:
(1) Saline+Water;
(2) 10 mg/kg of rhGAA+Water;
(3) 10 mg/kg of rhGAA+3 mg/kg of 1 DNJ-HCl;
(4) 10 mg/kg of rhGAA+30 mg/kg of 1 DNJ-HCl;

The rhGAA or saline was administered 30 minutes after administration of the 1-DNJ-HCl. GAA Activity was determined as generally described in Example 3. The results over 24 hours are shown in FIG. 6. The 1-DNJ-HCl inhibited the loss of enzyme activity post-administration, thereby increasing the in vivo half life of rhGAA. The in vivo half life of rhGAA increased from 1.4±0.2 hours (0 mg/kg of 1-DNJ- HCl) to 2.1±0.2 hours (3 mg/kg of 1-DNJ-HCl) and 3.0±0.4 hours (30 mg/kg of 1-DNJ-HCl).

Example 6: GAA Enzyme Activity in GAA KO Mouse

Three groups of GAA KO Mice were administered one of the following formulations:
 (1) Control (No Treatment);
 (2) 10 mg/kg of rhGAA;
 (3) 10 mg/kg of rhGAA and 100 mg/kg of 1-DNJ-HCl 30 minutes prior to rhGAA infusion, and every 8 hours after infusion for 48 hours.

Figure 7A:
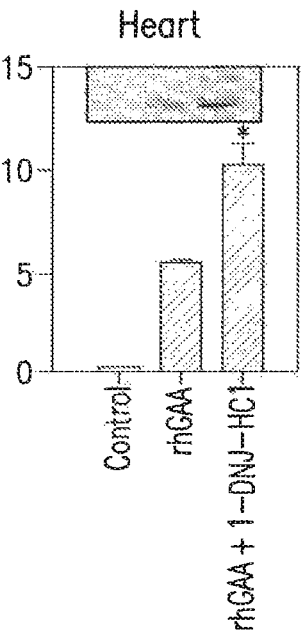
Figure 7B:
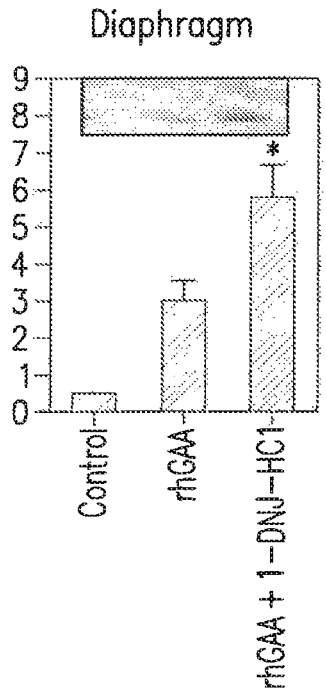

Heart and Diaphragm tissue homogenates were harvested and rhGAA activity was measured using the fluorogenic substrate (4-MUG). The results are shown in FIGS. 7A and 7B.

Figure 8:
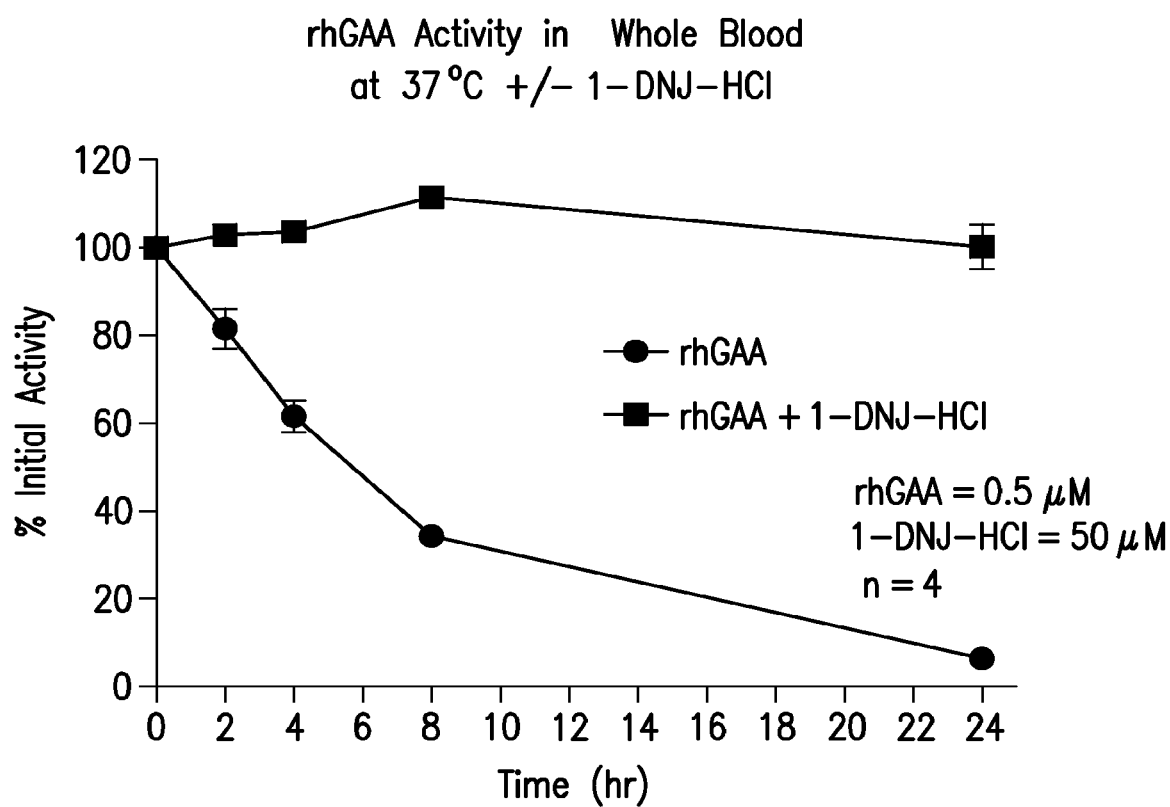

Example 7: 1-DNJ-HCl Stabilizes rhGAA and Prevents Enzyme Inactivation in Blood 1-DNJ-HCl was evaluated for its ability to stabilize rhGAA (e.g., Myozyme®) in whole (sodium citrate anti-coagulated) blood at 37° C. to mimic the environment that the ERT is exposed to during the multi-hour infusion. The results indicate that rhGAA is unstable under these conditions such that approximately 40% of the enzyme inactivated by 4 hrs, ~70% by 8 hrs and nearly 100% by 24 hrs as shown (red diamond line plot) in FIG. 8. These results suggest that a significant fraction of the rhGAA dose would likely be inactive because these infusions are typically more than 6 hrs, and in some instances 12 hrs. Moreover, since Myozyme® has a long plasma half-life (reported to be more than 3 hrs), there is a high probability that an appreciable amount of the enzyme remains in the circulation many hours after the infusion that would also be prone to inactivation. By contrast, when rhGAA was incubated with 50 µM 1-DNJ-HCl under the same experimental conditions, the enzyme remained completely active throughout the study (blue square line plot). These results indicate that 1-DNJ-HCl stabilized rhGAA and prevented enzyme inactivation in whole blood. Importantly, these data also indicate that the plasma proteins present in blood are not sufficient to prevent the loss of rhGAA enzyme activity whereas a pharmacological chaperone like 1-DNJ-HCl is able to prevent enzyme inactivation.

Figure 9:
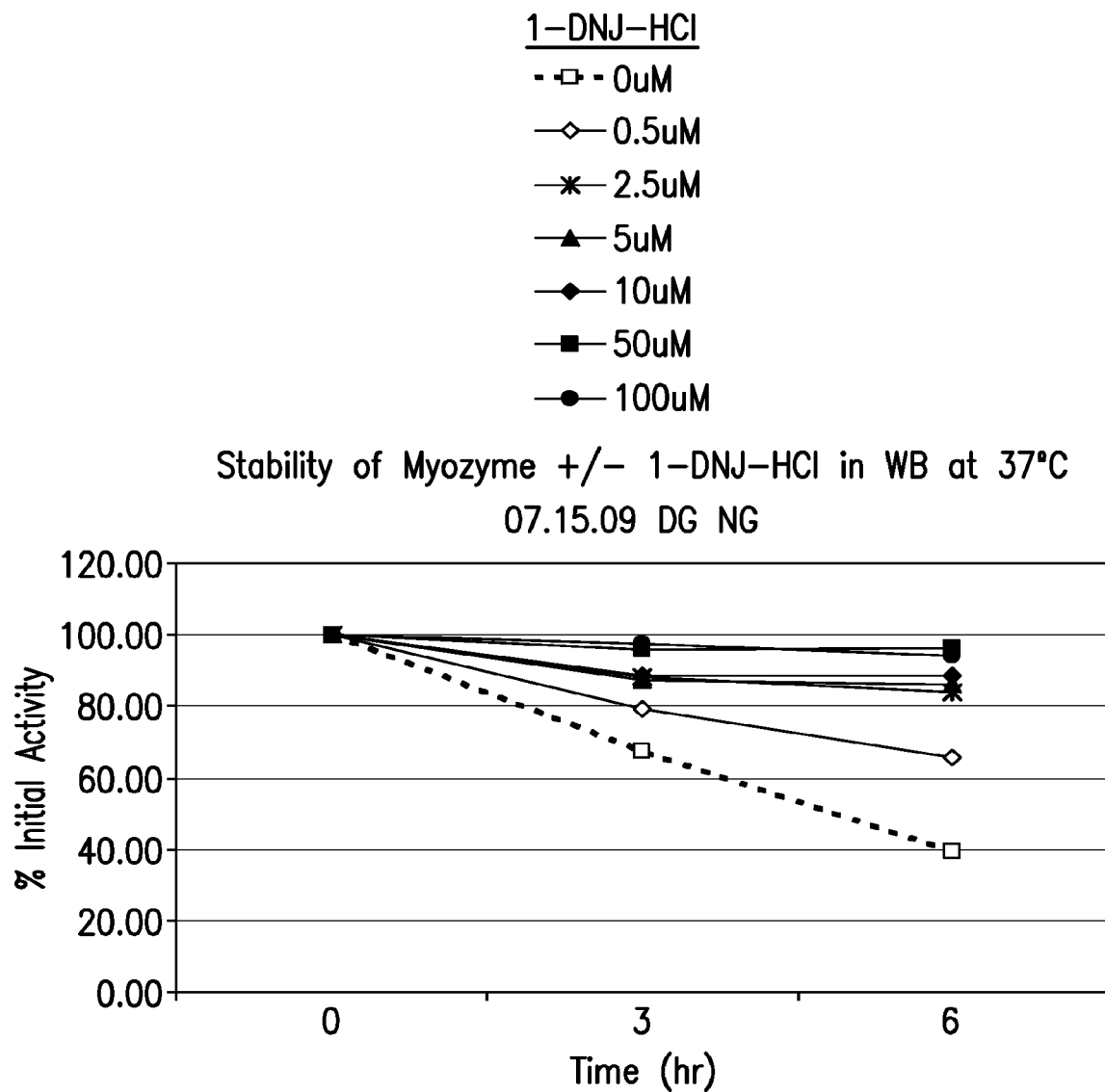
Figure 11A:
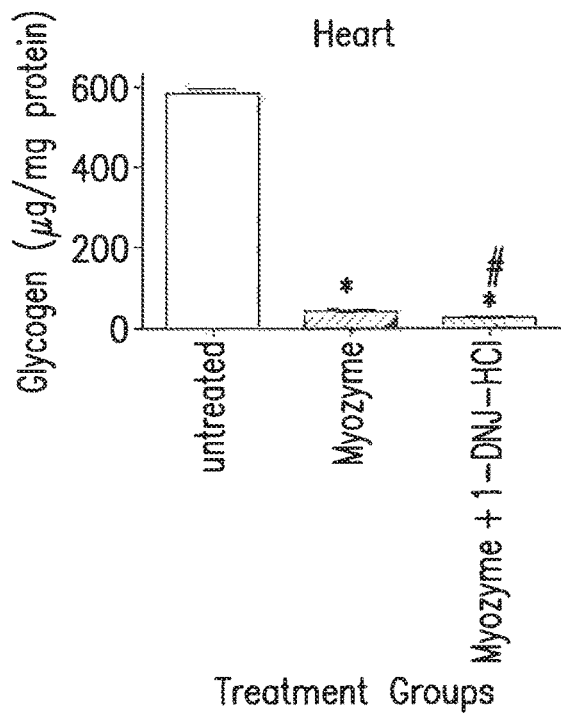
Figure 11B:
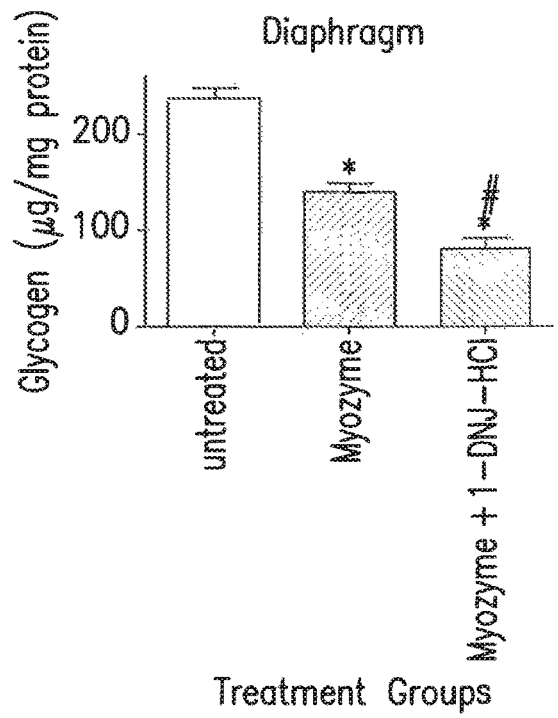
Figure 11C:
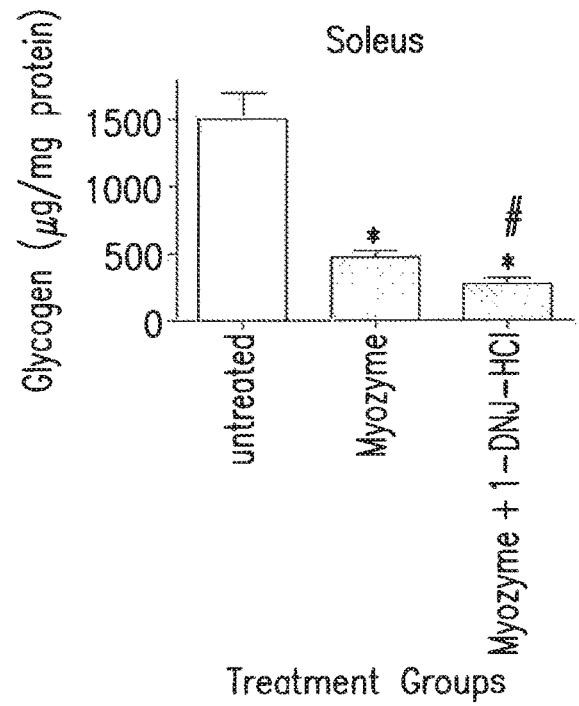
Figure 11D:
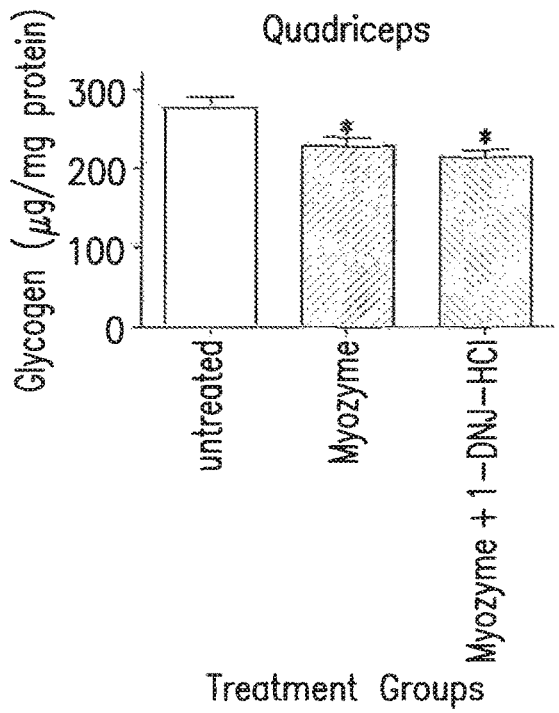

Example 8: 1-DNJ-HCl Stabilizes rhGAA and Prevents Enzyme Inactivation in Blood rhGAA measured in whole blood with varying concentrations of 1-DNJ-HCl (0-100 µM) to determine the minimum concentration of 1-DNJ-HCl that prevents rhGAA enzyme inactivation (FIG. 9). As expected, high 1-DNJ-HCl concentrations (50 and 100 µM) were best for stabilizing rhGAA and preventing enzyme inactivation. Interesting however, low 1-DNJ-HCl concentrations (as low as 2.5 µM) also maintained rhGAA activity with a loss of ~20% over a 6-hr time course. These results suggest that moderate 1-DNJ-HCl concentrations (e.g., 10-25 µM) may be adequate for stabilizing rhGAA in blood during infusions. Based on human plasma PK data, these concentrations are readily obtainable in the clinic.

Example 9: Myozyme® Co-Administered with 1-DNJ-HCl Resulted in Significantly Greater Tissue Glycogen Reduction in GAA KO Mice as Compared to Myozyme® Alone Twelve-week old male GAA KO mice were administered a single dose of Myozyme® (40 mg/kg) via bolus tail vein injection every other week for 8 weeks. To prevent anaphylaxis, before the third and fourth Myozyme® injection, diphenhydramine (10 mg/kg intraperitoneally) was administered 10 min before Myozyme® injection. In addition, mice received either water or 30 mg/kg of 1-DNJ-HCl administered via oral gavage 30 minutes prior to Myozyme® administration. Mice were euthanized 14 days after the last Myozyme® administration. The Experimental design is shown in FIG. 10.

Glycogen levels in heart, diaphragm, soleus, and quadriceps were then measured. Myozyme® co-administered with 1-DNJ-HCl resulted in significantly greater tissue glycogen reduction in GAA KO mice as compared to Myozyme® alone (FIGS. 11A, 11B, 11C, and 11D). Briefly, homogenates were prepared by homogenizing ~50 mg tissue for 3-5 seconds on ice with a microhomogenizer in 200 deionized water. Supernatants were heat denatured (99° C. for 10 min) to remove endogenous amyloglucosidase activity. Denatured lysates (4 µL) were then analyzed in duplicate by addition of 36 µL water with and without 10 µL of 800 U/mL of amyloglucosidase (Sigma Aldrich, St. Louis, Mo.) and incubated for 1 hour at 50° C. The reaction was stopped by inactivation at 100° C. for 10 min. Finally, 200 µL of glucose reagent (Sigma) was added absorbance read at 340 nm on Spectramax. A standard curve ranging from 5 µg/mL to 400 µg/mL Type III rabbit liver glycogen (Sigma) was run each day for conversion of absorbance to absolute glycogen units. Simultaneously, the amount of protein was determined in tissue homogenates using the Micro BCA Protein Assay (Pierce, Rockford, Ill.) following the manufacturer's instructions. The glycogen content of each sample was normalized to protein, and data were finally expressed as micrograms of glycogen per milligram of protein (µg/mg protein).

Example 10: DNJ Reduces Aggregation of Myozyme® in Compositions Comprising High Concentrations of Myozyme®

A liquid formulation comprising DNJ and GAA was prepared by dissolving DNJ in water to achieve a concentration of 10 mM DNJ. GAA was reconstituted in 1.8 ml water, and dialyzed overnight in phosphate buffered-saline (pH 7.4). 4.4 microliters of DNJ (10 mM) was then be added to 400 microliters of GAA, such that the GAA was at a concentration of 25 mg/ml.

Figure 12:
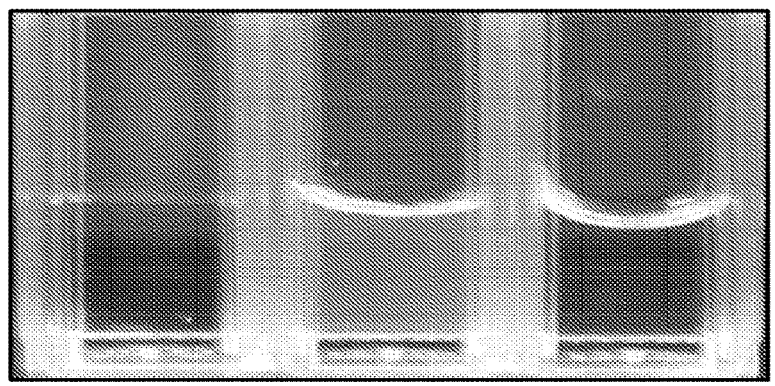

25 mg/mL Myozyme® was incubated with or without 1 mM DNJ in phosphate-buffered saline at pH 7.4. Aggregation of Myozyme® was assessed after incubation for 4 weeks at 37° C. As shown in FIG. 12, combining 1 mM DNJ with 25 mg/mL Myozyme® reduced aggregation of Myozyme®.

Example 11: DNJ Increases the Circulating Half-Life and Tissue Uptake of Myozyme®

Sprague-Dawley rats were administered 10 mg/kg Myozyme® or 30 mg/kg DNJ mixed with 10 mg/kg Myozyme® via tail vein. GAA activity was measured in plasma and quadriceps tissue. Baseline GAA activity in quadriceps was subtracted (~16 nmol/mg protein/hr) from the measured GAA following GAA or DNJ and GAA administration.

Figure 13:
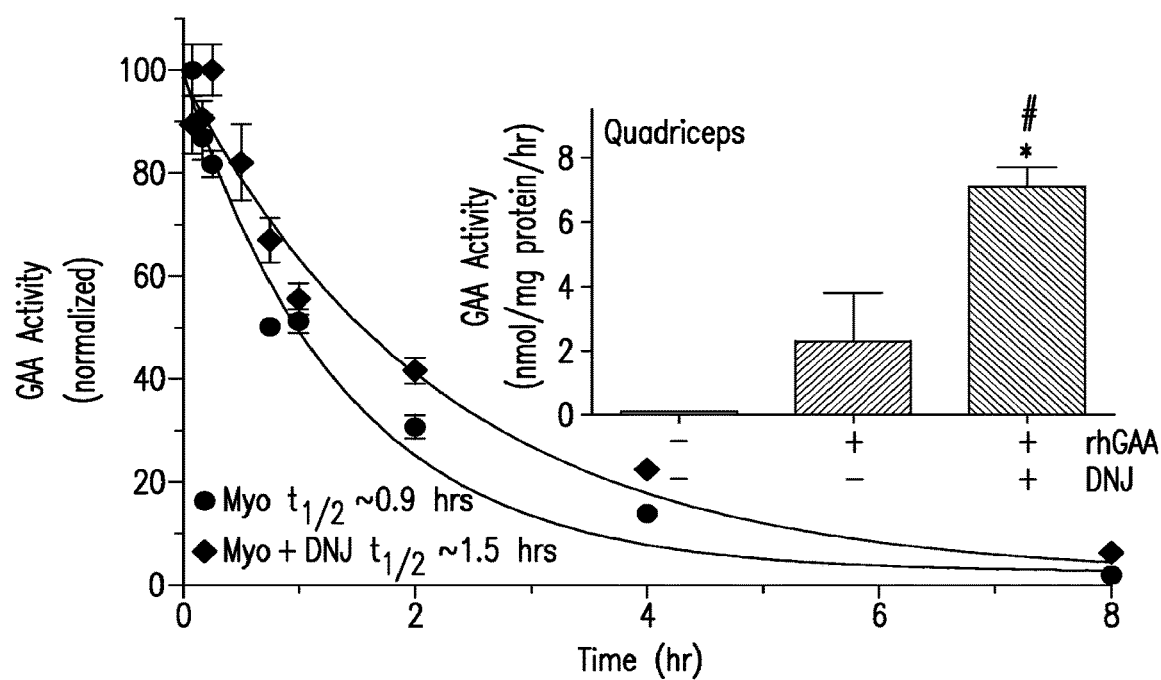
FIG. 13 shows that administering 30 mg/kg DNJ co-formulated with an amount equivalent to 10 mg/kg Myozyme® via tail vein injection increased the circulating plasma half-life and tissue uptake of Myozyme® in quadriceps.
Figure 14:
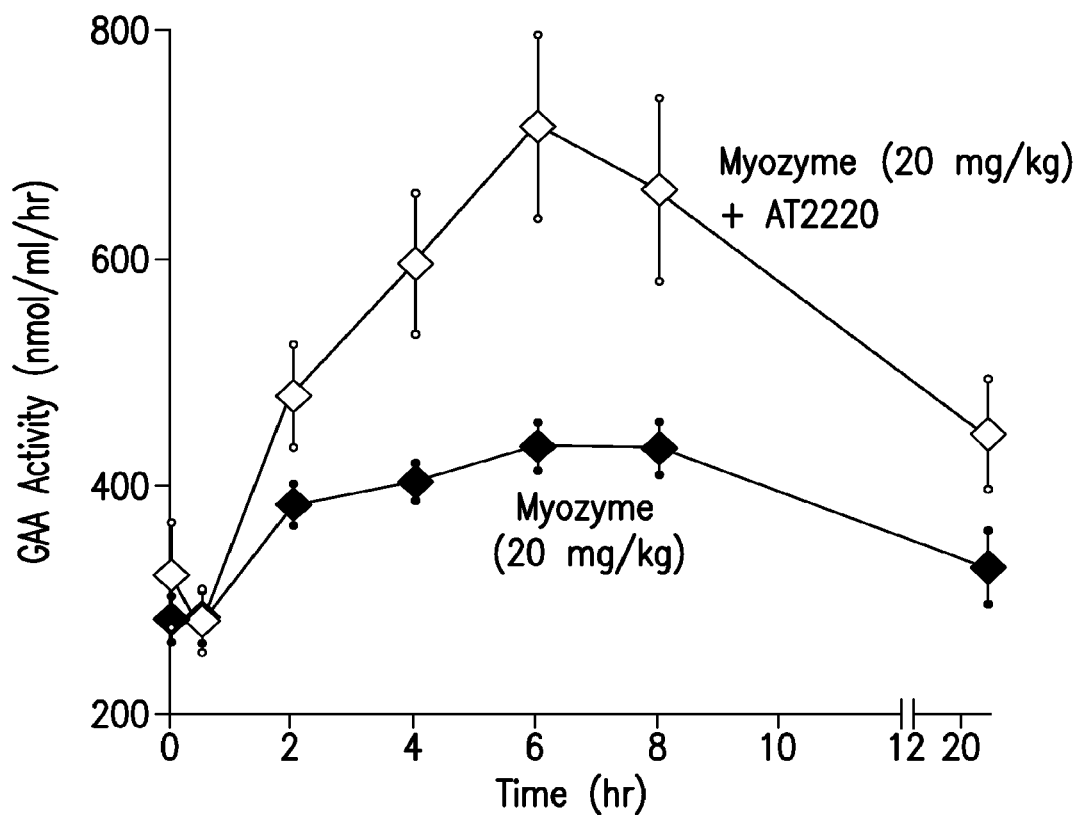
FIG. 14 shows that subcutaneous administration of DNJ co-formulated with 20 mg/kg Myozyme® increased the circulating levels of rhGAA compared to administration of 20 mg/kg Myozyme® without DNJ.
Figure 15:
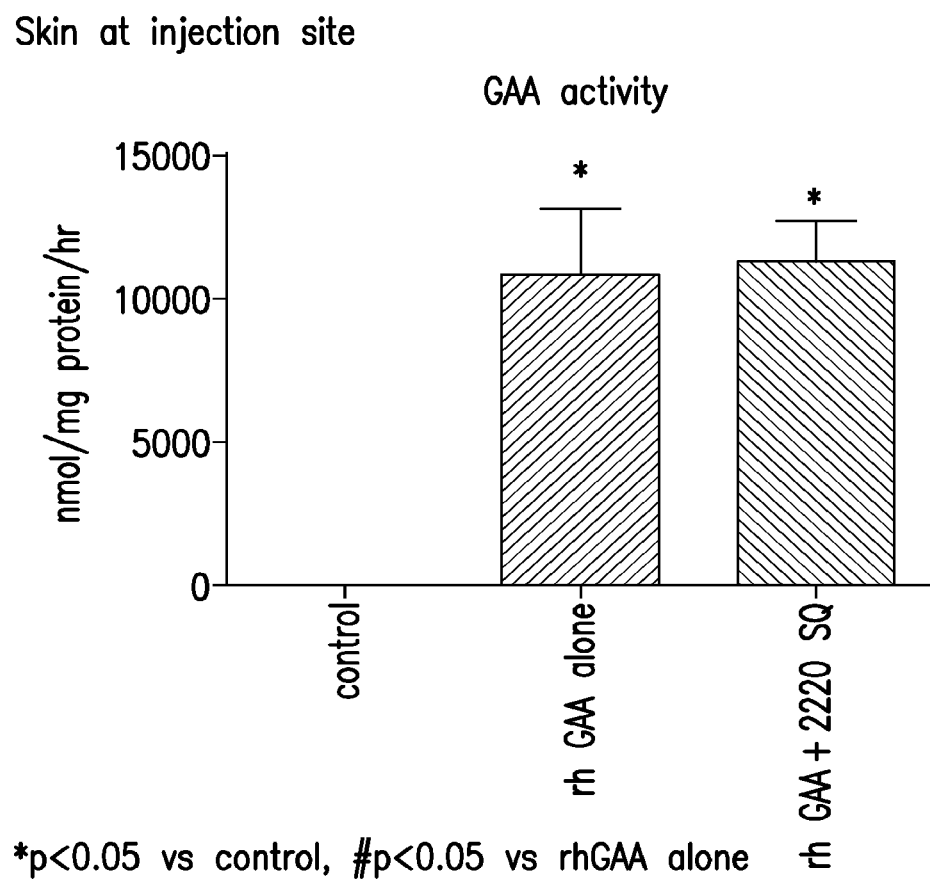
FIG. 15 shows rhGAA activity in skin at the injection site 3 days following the last subcutaneous administration of rhGAA or a co-formulation of rhGAA and 1-DNJ to mouse, as described in Example 13.

As shown in FIG. 13, administering 30 mg/kg DNJ with 10 mg/kg Myozyme® via tail vein increased the circulating plasma half-life and tissue uptake of Myozyme® in quadriceps.

Example 12: Solubility of Lumizyme® in the Presence of 1-DNJ

The solubility of Lumizyme® (alglucosidase alpha) in the presence of 1-DNJ and different excipients was examined.

Method

A vial of Lumizyme® containing 52.5 mg protein, 210 mg mannitol, 0.5 mg polysorbate 80, 9.9 mg $Na_2HPO_4 \times 7H_2O$, and 31.2 mg $NaH_2PO_4 \times H_2O$ was dissolved in a minimal volume of water (1 mL added) yielding 1.2 mL of protein solution. Five 240-µL aliquots (each containing 10.5 mg protein) were transferred to Amicon Ultra 0.5 mL 30 kDa cutoff centrifugal filter devices and centrifuged for 10 min at 14,000×g in an Eppendorf centrifuge to obtain about 50 µL of retentate.

The original excipients present in the composition, i.e., mannitol and polysorbate 80 were exchanged for new excipients to test protein solubility (keeping the same buffer conditions). The following excipient solutions were prepared for the exchange using the original phosphate buffer:
1. PEG 400 (5% w/v)
2. Arginine (100 mM)
3. Arginine (50 mM)+Glutamic acid (50 mM)
4. Proline (250 mM)
5. Gamma-cyclodextrin (10%)

All samples contained the small molecule ligand 1-deoxynojirimycin hydrochloride (1-DNJ-HCl, AT2220 HCl, 2220 HCl) at a ratio 1:1 (w/w) of the ligand to protein, except for sample 2 (100 mM arginine) which contained the ligand at a reduced 1:5 (w/w) ligand to protein ratio.

For exchanging excipients, 5.2 mg $Na_2HPO_4$ and 27.1 mg $NaH_2PO_4$ were dissolved in 10.3 mL water to prepare the washing/excipient exchange phosphate buffer of approximately 26 mM. A volume of 8 mL of the buffer for excipient exchange was supplemented with 160 mg/mL of the small molecule ligand (to prepare excipient 1, 3, 4 and 5 solutions), while 2 mL was supplemented with 32 mg/mL ligand for excipient 2 (100 mM Arginine). Each of the excipients were dissolved in 2 mL of this buffer at the concentrations listed above.

An excipient solution was added to each separate filter device to achieve a total volume of 0.5 mL. Each filter device was centrifuged for 15 min at 14,000×g in a bench top Eppendorf centrifuge to retain approximately 25 µL. The units were re-filled with the same excipient solution to 0.5 mL and centrifuged again (this process was repeated 2 times). This procedure efficiently replaced mannitol and polysorbate 80 with excipients described above, diluting the original constituents by about 1:1000. All filtrates for each excipient were collected and examined for any protein leaks through the filter.

Each centrifugal filter device was inverted in a clean tube, and the concentrated protein solution was collected from each filter device by centrifugation for 2 min at 1000×g. The volume of each sample was determined (664, corresponding to a target protein concentration of 160 mg/mL), and it was confirmed that no visible precipitate was observable in each sample. Samples were transferred back to their respective filter devices and centrifuged for an additional 5 min. Samples were then collected by inversion of the filters into clean tubes and centrifuging for 2 min at 1000×g to yield about 37 µL of retentate (corresponding to >280 mg/mL protein based on a total initial concentration of 10.5 mg protein).

The samples were vortexed and incubated for 1 hr at room temperature to equilibrate liquid and solid phases followed by centrifugation for 10 min at 14,000×g. Again, no visible precipitate was observed. Two-three 10 µL aliquots were taken from the supernatant of each sample (depending on available volume of the liquid phase), and diluted 1:1000 in two steps. Protein concentration was measured by UV absorbance at 280 nm, and the maximum protein solubility was calculated according to a highly reproducible calibration curve. The calibration curve was prepared by dissolving 6.8 mg of Myozyme® (alglucosidase alpha) lyophilized powder (containing 1.16 mg protein) in 1.16 mL of water followed by a serial dilution in deionized water. Absorbance was measured at 280 nm in a 1 cm light-pass quartz semi-micro cuvette using 0.5 mL aliquots.

Results:

As shown in Table 1, the excipients tested in this study increased the solubility of the protein in the presence of a small molecule ligand, 1-DNJ-HCl. The highest value observed was for the mixture of arginine and glutamic acid (242 mg/mL), the lowest for gamma-cyclodextrin (114 mg/mL). The solubility of the protein without the added excipients was determined to be about 80 mg/mL. Without being bound by any theory, the increase in solubility may be due to efficient interactions of amino acid excipients with the protein surface hydrophobic and hydrophilic sites, which competitively block protein-protein associations.

TABLE 1

Solubility of Lumizyme ® (alglucosidase alpha) in the presence of the ligand 1-DNJ-HCl and selected excipients.

| Excipient | Concentration | 1-DNJ-HCl (mg/mL) | Protein solubility (mg/mL) |
| --- | --- | --- | --- |
| PEG400 | 5% (w/v) | 160 | 158 |
| Arginine | 100 mM | 32 | 201 |
| Arginine + Glutamic acid | 50 mM + 50 mM | 160 | 242 |
| Proline | 250 mM | 160 | 195 |
| Gamma-cyclodextrin | 10% (w/v) | 160 | 114 |

Example 13: The Effect of Repeat Subcutaneous Dosing of Co-Formulated rhGAA and 1-DNJ on Tissue Uptake and Glycogen Reduction in GAA KO Mice The present study examined whether GAA knockout mice (GAA KO) tolerate repeat subcutaneous (SQ) injections of rhGAA or a co-formulation of rhGAA and 1-DNJ, whether the repeated SQ injections of rhGAA increase tissue uptake of rhGAA and reduce glycogen levels in the GAA KO mice, and whether the repeated SQ injections of a co-formulation of rhGAA and 1-DNJ increase tissue uptake of rhGAA and reduce glycogen levels compared to SQ injections of rhGAA alone.

Methods 12-week old male GAA KO mice in groups of 7 were used in the present study. Each group of mice was administered one of the following treatments:
(1) Saline only (no drug control);
(2) Lumizyme® alone (20 mg/kg) delivered subcutaneously (SQ); or (3) Co-formulated Lumizyme® (20 mg/kg) and 1-DNJ (30 mg/kg) SQ.

Each of the treatments were administered to their respective treatment group for a period of 2 weeks. The treatments were administered on Monday and Thursday of each week. SQ injections were administered between the shoulder blades of each mouse receiving treatment. A total of 4 doses was administered to each study animal. Diphenhydramine was administered intraperitoneally (IP) before the 3rd and 4th doses.

rhGAA and glycogen levels were determined according to the following sampling protocol. Blood was taken from each study animal after the 4th dose for plasma pharmacokinetic analysis. GAA activity, Western blots, and 1-DNJ levels were determined for plasma samples taken 2 and 4 hours after the last SQ dose.

Tissue samples were collected to determine rhGAA uptake 3 days following the last dose of the study (i.e., 3 days post dose 4). Tissue samples included heart, diaphragm, tongue, brain, spleen, liver, biceps, triceps, quadriceps, soleus, gastrocnemius, ventral skin and dorsal skin from the SQ injection site. Tissue samples were also collected to determine glycogen concentration 14 days following the last dose of the study (i.e., 14 days post dose 4). A summary of the treatments administered to the test subjects, and the timing of sample collection is shown in Table 2.

TABLE 2

Treatments administered and sample collection times of the present study.

| Group | Lumizyme® alone SQ, mg/kg | Co-formulation of Lumizyme® + 1-DNJ SQ, mg/kg | Plasma timepoint, hr | Necropsy day |
|---|---|---|---|---|
| 1 | 0 | 0 | 2 | 3 |
| 2 | 0 | 0 | 4 | 14 |
| 3 | 20 | 0 | 2 | 3 |
| 4 | 20 | 0 | 4 | 14 |
| 5 | 0 | 20 L + 30 1-DNJ | 2 | 3 |
| 6 | 0 | 20 L + 30 1-DNJ | 4 | 14 |

Dosing was administered each Monday and Thursday for 2 weeks for a total of 4 administrations. There were no deaths in any group.

Results

Tissue rhGAA and Glycogen

FIGS. 15-25 show GAA activity 3 days following the final treatment dose, and glycogen levels 14 days following the final treatment dose in tissue samples taken from animals receiving one of the three treatments. For most of the tissues tested, co-formulating rhGAA with 1-DNJ significantly increased rhGAA uptake and activity in the tissues tested compared to administering rhGAA alone. Additionally, following treatment with rhGAA, or the co-formulation of rhGAA and 1-DNJ, rhGAA activity was high at the site of SQ injection, in ventral skin and in forelimb muscles 3 days following the final treatment dose. rhGAA activity was higher in liver than in all muscles tested except for forelimbs.

Furthermore, as described in Table 3, rhGAA levels achieved with the co-formulation of 1-DNJ and rhGAA (Lumizyme®) administered SQ were either as high or higher (in a majority of tissues) compared to levels achieved by administering rhGAA (Myozyme®) intravenously alone.

TABLE 3 rhGAA activity uptake (nmol/mg/hr) of a co-formulation of rhGAA (Lumizyme ®) and 1-DNJ administered SQ compared to rhGAA (Myozyme ®) administered alone intravenously (IV) and Lumizyme ® administered alone SQ.

| Tissue | Myozyme® IV[1] | Lumizyme® SQ[2] | Lumizyme® + 1-DNJ co-formulation, SQ[2] |
|---|---|---|---|
| Skin | 27.1 | 75 | 118 |
| Heart | 1.8 | 1.9 | 3.0 |
| Diaphragm | 7.1 | 4.2 | 6.1 |
| Tongue | 12.4 | 2.7 | 5.5 |
| Triceps | 3.9 | 88.0 | 155 |
| Biceps | 10.1 | 56.0 | 60 |
| Quadriceps | 6.9 | 2.1 | 5.7 |
| Gastrocnemius | 17.9 | 2.0 | 3.1 |
| Soleus | 8.0 | 2.7 | 2.2 |

[1]GAA KO mice were given 4 doses of Myozyme (20 mg/kg) IV bolus at 2 week intervals.
[2]GAA KO mice were given 4 doses of Lumizyme (20 mg/kg) +/− 1-DNJ (30 mg/kg) SQ at 3-4 day intervals (Mon and Thu).
Enzyme activity uptake data for both studies assessed 3 days after the last (4th) dose.

With regard to the glycogen levels detected in the tissue samples, the magnitude of reduction in glycogen was correlated with rhGAA uptake in some tissues. Heart, tongue, and ventral skin showed a correlation between improved uptake of rhGAA and improved glycogen reduction with the rhGAA+1-DNJ co-formulation over rhGAA alone. Without being bound by any theory, high rhGAA enzyme activity in some tissue lysates could be from enzyme that is in the tissue (e.g., fat, lymph, blood vessels) but that has not yet been taken into the cells and lysosomes. Additionally, without being bound by any theory, there may be an abundance of cytoplasmic glycogen that is not available to the lysosomal enzyme but is detectable in whole cell lysates.

Plasma rhGAA

To determine whether 1-DNJ present in plasma samples from animals treated with the co-formulation inhibited rhGAA in the samples, rhGAA activity was determined by incubating rhGAA from the plasma samples with GAA substrate for 1 hour, and determining enzyme activity based on substrate metabolism. Samples were then re-analyzed by incubating the samples for 3 hours with substrate to allow for dissociation of 1-DNJ from the enzyme, and thereby reverse any enzyme inhibition caused by 1-DNJ. No substantial changes were seen in results between the two assay formats.

FIGS. 26, 27A, 27B, 28A, and 28B show plasma rhGAA activity and protein concentration in samples collected 2 and 4 hours following the final treatment dose. 2 hours after the final SQ treatment dose, higher rhGAA activity and protein concentrations were detectable in plasma (i.e., activity assay and Western blot, respectively) when 1-DNJ was administered with rhGAA in the co-formulation than when rhGAA was administered alone. 4 hours after the final SQ treatment dose, the plasma rhGAA levels remained elevated in the mice treated with the co-formulation, while plasma rhGAA levels from mice treated with rhGAA alone increased compared to the levels in the 2 hour samples.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, product descriptions, GenBank Accession Numbers, and protocols are cited throughout this application, the disclosures of which are incorporated herein by reference in their entireties for all purposes.

What is claimed is:

1. A method of treating Pompe disease in a subject comprising administering
   (i) a first composition comprising an active site-specific chaperone selected from the group consisting of 1-deoxynojirimycin or a pharmaceutically acceptable salt thereof and n-butyl-deoxynojirimycin or a pharmaceutically acceptable salt thereof, and
   (ii) a second composition comprising acid α-glucosidase, wherein the active site-specific chaperone of the first composition is present in an amount from about 20 mg/mL to about 200 mg/mL, and wherein the acid α-glucosidase of the second composition is present in an amount from about 5 mg/mL to about 500 mg/mL.

2. The method of claim 1, wherein the acid α-glucosidase of the second composition is present in an amount from about 5 mg/mL to about 250 mg/mL.

3. The method of claim 2, wherein the acid α-glucosidase of the second composition is present in an amount from about 10 mg/mL to about 200 mg/mL.

4. The method of claim 1, wherein the acid α-glucosidase of the second composition is present in an amount of about 25 mg/mL.

5. The method of claim 1, wherein at least one of the first composition and the second composition is a liquid formulation.

6. The method of claim 1, wherein at least one of the first composition and the second composition further comprises an excipient.

7. The method of claim 6, wherein the excipient is selected from the group consisting of polyethylene glycol 400, arginine, glutamic acid, proline, gammacyclodextrin, and combinations thereof.

8. The method of claim 1, wherein at least one of the first composition and second composition further comprises a buffer.

9. The method of claim 8, wherein the buffer is selected from the group consisting of citrate buffer, acetate buffer, bicarbonate buffer, phosphate buffer, and combinations thereof.

10. The method of claim 1, wherein the active site-specific chaperone of the first composition is n-butyl-deoxynojirimycin or a pharmaceutically acceptable salt thereof.

11. The method of claim 1, wherein the active site-specific chaperone of the first composition is 1-deoxynojirimycin or a pharmaceutically acceptable salt thereof.

12. The method of claim 1, wherein at least one of the first composition and the second composition are administered independently by subcutaneous injections.

13. The method of claim 12, wherein at least one of the first composition and the second composition are administered independently with separate subcutaneous injections of 1, 2, 3, 4, 5, 6, 7, 8, 9 or 10 milliliters.

14. The method of claim 1, wherein at least one of the first composition and the second composition are administered intravenously as separate independent injections.

15. The method of claim 1, wherein the first composition is administered orally and the second composition is administered intravenously.

* * * * *